US012247195B2

United States Patent
Noggle et al.

(10) Patent No.: US 12,247,195 B2
(45) Date of Patent: *Mar. 11, 2025

(54) MICROFLUIDIC SYSTEM AND METHOD OF USE THEREOF

(71) Applicant: New York Stem Cell Foundation, Inc., New York, NY (US)

(72) Inventors: Scott Noggle, New Rochelle, NY (US); Stephen Chang, Poway, CA (US)

(73) Assignee: New York Stem Cell Foundation, Inc., New York, NY (US)

( * ) Notice: Subject to any disclaimer, the term of this patent is extended or adjusted under 35 U.S.C. 154(b) by 294 days.

This patent is subject to a terminal disclaimer.

(21) Appl. No.: 17/987,073

(22) Filed: Nov. 15, 2022

(65) Prior Publication Data

US 2023/0144965 A1 May 11, 2023

Related U.S. Application Data

(63) Continuation of application No. 16/462,047, filed as application No. PCT/US2017/062344 on Nov. 17, 2017, now Pat. No. 11,542,465.

(Continued)

(51) Int. Cl.
*C12M 1/00* (2006.01)
*B01L 3/00* (2006.01)
(Continued)

(52) U.S. Cl.
CPC .......... *C12M 47/04* (2013.01); *B01L 3/5027* (2013.01); *F16K 99/0003* (2013.01);
(Continued)

(58) Field of Classification Search
CPC .......... B01L 2200/0647; B01L 3/5027; B01L 3/502761; F16K 2099/0086;
(Continued)

(56) References Cited

U.S. PATENT DOCUMENTS

2004/0224380 A1 11/2004 Chou et al.
2006/0253192 A1 11/2006 Atala et al.
(Continued)

FOREIGN PATENT DOCUMENTS

JP 2016-67330 A 5/2016
WO WO-2016/100227 A1 6/2016
(Continued)

OTHER PUBLICATIONS

Bissoyi, A. et al., "Enhanced cryopreservation of MSCs in microfluidic bioreactor by regulated shear flow", Scientific Report, 6:35416, Oct. 17, 2016, pp. 2-14.
(Continued)

*Primary Examiner* — Jennifer Wecker
(74) *Attorney, Agent, or Firm* — Goodwin Procter LLP

(57) ABSTRACT

This invention concerns an integrated microfluidic system that utilizes microfluidic chip technology to receive a patient sample including cells, expand the cells, reprogram the expanded cells and then store the reprogrammed cells in a microfluidic chip. These microfluidic chips with stored reprogrammed cells may then be used in scenarios of genetic differentiation into specific cell types. Overall this system and workflow is suitable as a hospital based device that will allow the generation of iPSCs from every patient for downstream diagnostic or therapeutic use.

22 Claims, 12 Drawing Sheets

Related U.S. Application Data

(60) Provisional application No. 62/424,208, filed on Nov. 18, 2016.

(51) Int. Cl.
*F16K 99/00* (2006.01)
*G01N 15/02* (2024.01)
*G01N 15/01* (2024.01)
*G01N 15/10* (2024.01)

(52) U.S. Cl.
CPC ...... *G01N 15/02* (2013.01); *F16K 2099/0086* (2013.01); *G01N 15/01* (2024.01); *G01N 2015/1006* (2013.01)

(58) Field of Classification Search
CPC ... F16K 99/0003; C12M 23/16; C12M 23/58; C12M 41/48; C12M 47/04; G01N 15/01; G01N 15/02; G01N 2015/1006
See application file for complete search history.

(56) References Cited

U.S. PATENT DOCUMENTS

| | | | |
|---|---|---|---|
| 2010/0003222 A1 | 1/2010 | Yayon et al. | |
| 2011/0003324 A1 | 1/2011 | Durack | |
| 2012/0258488 A1 | 10/2012 | Abilez et al. | |
| 2012/0329151 A1 | 12/2012 | Baskar et al. | |
| 2013/0345094 A1 | 12/2013 | Noggle et al. | |
| 2015/0159132 A1 | 6/2015 | Li et al. | |

FOREIGN PATENT DOCUMENTS

| | | |
|---|---|---|
| WO | WO-2016/191332 A2 | 12/2016 |
| WO | WO-2017/040548 A1 | 3/2017 |

OTHER PUBLICATIONS

European Search Report issued May 6, 2020 of International Application No. PCT/US2017/62344.

Hassan et al., "A Microfluidic Biochip for Complete Blood Cell Counts at the Point-of-Care," *Singap. World Sci.* (2005), 3(4):201-213.

International Search Report and Written Opinion of PCT/US2017/62344 dated Feb. 13, 2018, 27 pages.

Jonczyk et al., "Living Cell Microarrays: An Overview of Concepts," *Microarrays* (2016), 5(11):1-29.

Luni, C. et al., "High-efficiency cellular reprogramming with microfluidics", Nat. Methods, vol. 13, No. 5, Apr. 18, 2016, pp. 446-452.

Pamies et al., "Good Cell Culture Practice for Stem Cells and Stem-Cell-Derived Models," t4 Workshop Report, Altex Online First, Aug. 23, 2016, (4):1-44.

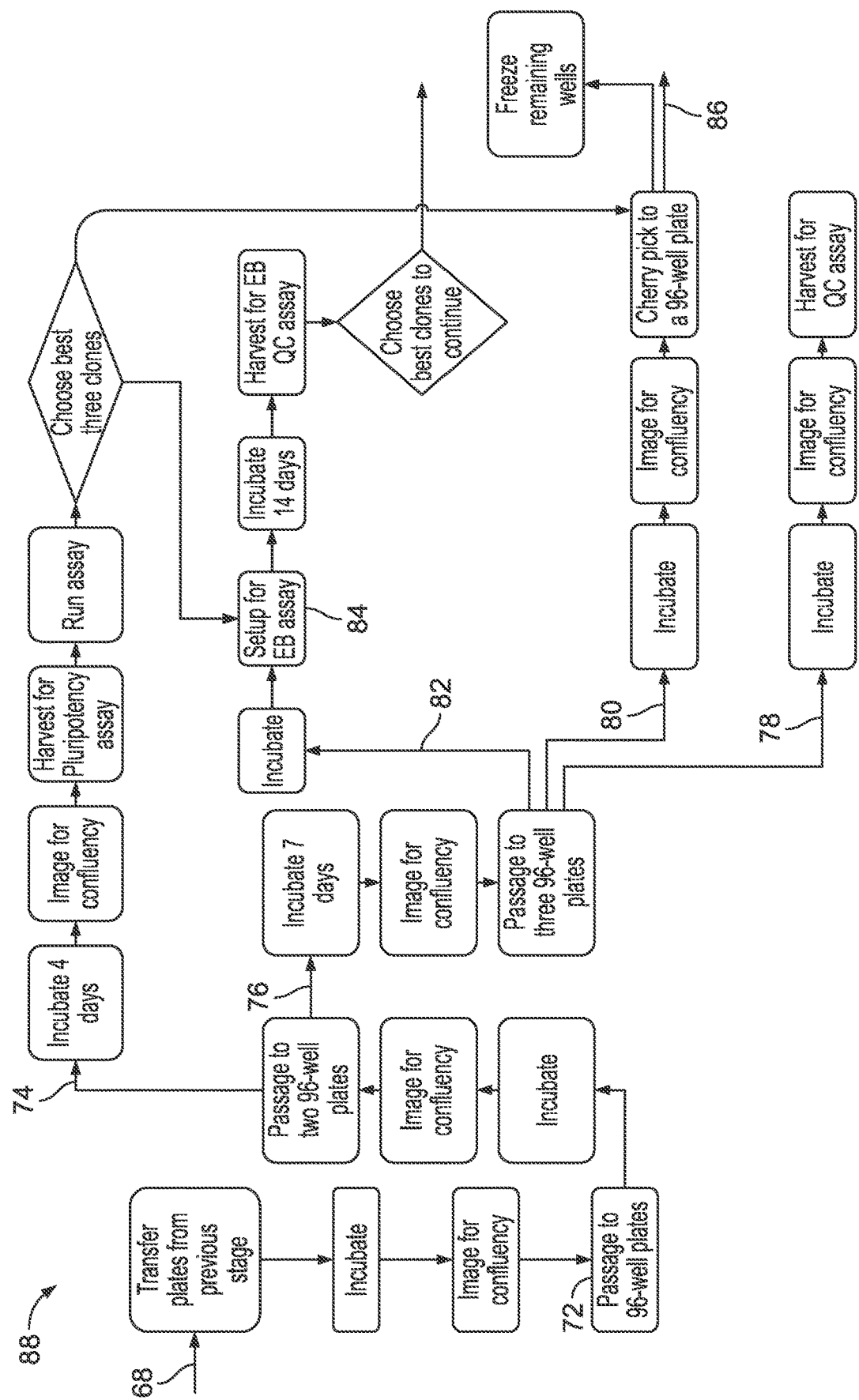
FIGURE 6B1

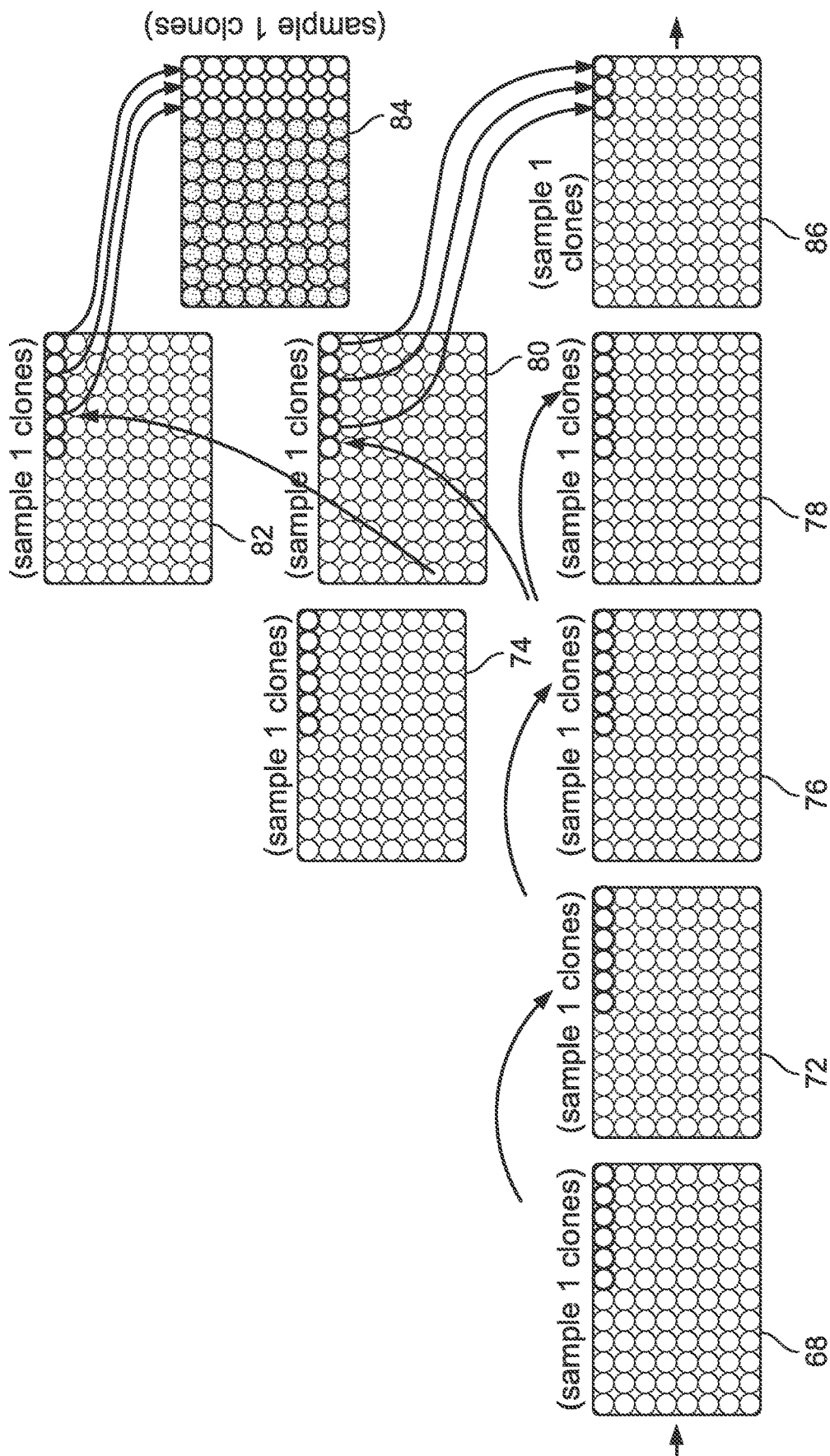
FIGURE 6B2

MICROFLUIDIC SYSTEM AND METHOD OF USE THEREOF

CROSS-REFERENCE TO RELATED APPLICATIONS

This application is a continuation of U.S. Ser. No. 16/462,047, filed May 17, 2019, which is a national stage application of International Application No. PCT/US2017/062344, filed Nov. 17, 2017, which claims benefit of priority under 35 U.S.C. § 119(e) of U.S. Ser. No. 62/424,208, filed Nov. 18, 2016, the entire contents of which is incorporated herein by reference in its entirety.

BACKGROUND

Field of the Invention

The invention relates generally to the field of microfluidic devices and more specifically to a microfluidic system and method for reprogramming, expanding, storing and optionally differentiating cells.

Background Information

Microfluidic systems are important in medical diagnostics and biotechnology research. Components of such systems include networks of very small wells and channels, through which liquids can deliver and combine precisely-controlled amounts of chemicals, cells, and molecules. The systems are used for a variety of tasks including mixing reagents, isolation and study of biomolecules, and sequestering and sorting living cells. To accomplish the precise transfer, mixing, and accurate metering that is required, microfluidic chips and substrates require complex control machinery such as micro-valves and pumps built into the chip, as well as pneumatic actuators, electronic solenoids, pneumatic actuators, robotic controllers, and the complex computer programs and systems that are required to control those devices.

The use of microfluidic devices provides many advantages over classical benchtop methods, including for example, an unrivaled economy of scale, as well as a high degree of parallelization and integration. As technology advances, microfluidic devices are becoming increasingly small in size and increasingly capable of performing multiple tasks. For example, microfluidic approaches have independently been proposed for cell segregation and isolation, cell culture, cellular differentiation, as well as screening for cellular reprogramming factors.

Stem cells are unspecialized cells that self-renew for long periods through cell division, and can be induced to differentiate into cells with specialized functions, i.e., differentiated cells. These qualities give stem cells great promise for use in therapeutic applications to replace damaged cells and tissue in various medical conditions. Embryonic stem (ES) cells are derived from the blastocyst of an early stage embryo and have the potential to develop into endoderm, ectoderm, and mesoderm (the three germ layers) (i.e., they are "pluripotent"). In vitro, ES cells tend to spontaneously differentiate into various types of tissues, and the control of their direction of differentiation can be challenging. There are unresolved ethical concerns that are associated with the destruction of embryos in order to harvest human ES cells. These problems limit their availability for research and therapeutic applications.

Adult stem (AS) cells are found among differentiated tissues. Stem cells obtained from adult tissues typically have the potential to form a more limited spectrum of cells (i.e., "multipotent"), and typically only differentiate into the cell types of the tissues in which they are found, though recent reports have shown some plasticity in certain types of AS cells. They also generally have a limited proliferation potential.

Induced pluripotent stem cells (iPSC or iPSCs) are produced by laboratory methods from differentiated adult cells. iPSCs are widely recognized as important tools, e.g., for conducting medical research. Heretofore, the technology for producing iPSCs has been time-consuming and labor-intensive. Differentiated adult cells, e.g., fibroblasts, are reprogrammed, cultured, and allowed to form individual colonies which represent unique clones. Previously, identifying these types of cells has been difficult because the majority of the cells are not fully-reprogrammed iPSC clones. The standard is for iPSC clones to be selected based on the morphology of the cells, with desirable colonies possessing sharply demarcated borders containing cells with a high nuclear-to-cytoplasmic ratio. When clones are identified, they are manually-picked by micro-thin glass tools and cultured on "feeder" layers of cells typically, Murine Embryonic Fibroblasts (MEF). This step is performed typically at 14-21 days post-infection with a reprogramming vector. Then the clones are expanded for another 14-21 days or more, prior to undergoing molecular characterization.

Others have focused on developing techniques to rapidly and more accurately identify and characterize fully-reprogrammed adult fibroblasts and their downstream differentiation potential (Bock et al., 2011, *Cell* 144: 439-452; Boulting et al., 2011, *Nat Biotechnol* 29: 279-286). Also see, for example, co-owned U.S. Ser. No. 13/159,030, filed on Jun. 13, 2011, describing the use of Fluorescence Activated Cell Sorting (FACS) to identify and live sort unique subpopulations of s as defined by unique expression patterns of surface proteins.

Thus, stem cells are an attractive source of cells for therapeutic applications, medical research, pharmaceutical testing, and the like. The use of patient-specific stem cells and reprogrammed somatic cells makes immunologically compatible cell replacement strategies extremely desirable for several medical treatments such as treatment of cancer and neuronal diseases to name a few. However, there remains a longstanding need in the art for improved microfluidic devices and methods for processing patient specific-cells utilizing an integrated approach in which multiple tasks are performed using an automated and rapid approach to go from initially processing a patient's blood to individualized treatment of the same patient using patient-specific stem cells and reprogrammed somatic cells.

SUMMARY OF THE INVENTION

The present invention provides a microfluidic based system and methods utilizing the system to process biological samples to provide a time and cost efficient workflow to the laboratory and/or medical based environment. The overall workflow is capable of providing patient-specific treatments.

Accordingly, in one aspect, a microfluidic system for processing a biological sample is provided. The system includes one or more microfluidic units operable to perform a number of sample processing steps such that cells from the sample, or cells derived from the sample may be stored and catalogued and eventually utilized to treat a patient from which the sample was taken. The microfluidic units are operable to isolate cells from the sample, expand the isolated cells and reprogram the cells. The system also includes microfluidic functionality to differentiate the reprogrammed cells to a desired cell type for use in treating the patient. At any point in the process the system includes functionality for storing and cataloging cells. Additionally, the system is operable to perform analysis of the cells at any stage of processing to make qualitative and quantitative assessments of cells.

In embodiments, the system includes one or more computer memory modules containing instructions for controlling the processing functions along with one or more computer processor modules configured to execute the instructions.

In another aspect, the invention provides a method for processing a biological sample utilizing the microfluidic bases system of the disclosure. The method includes applying the sample to the system and performing the processing steps on the sample to produce reprogrammed cells and/or cells of a desired cell type derived from the reprogrammed cells.

In another aspect, the invention provides a method of treating a disease or disorder in a subject utilizing the microfluidic based system of the disclosure. The method includes: a) obtaining a sample from the subject; b) applying the sample to the system; c) processing the sample with the system; and d) administering processed cells to the subject, thereby treating the disease or disorder in the subject.

In still another aspect, the invention provides a pharmaceutical composition including cells processed by the microfluidic system, or a cellular fraction thereof, and optionally containing a pharmaceutically acceptable excipient.

In yet another aspect, the invention provides a cell bank. The cell bank includes one or more populations of cells which are processed by the system of the disclosure. In embodiments, each cell population is catalogued and stored at an appropriate temperature for future use.

BRIEF DESCRIPTION OF THE FIGURES

FIGS. 6A-6C show examples of a flow of patient samples through multi-well tissue culture plates during an automated reprogramming process in one embodiment of the invention.

DETAILED DESCRIPTION

Figure 1:
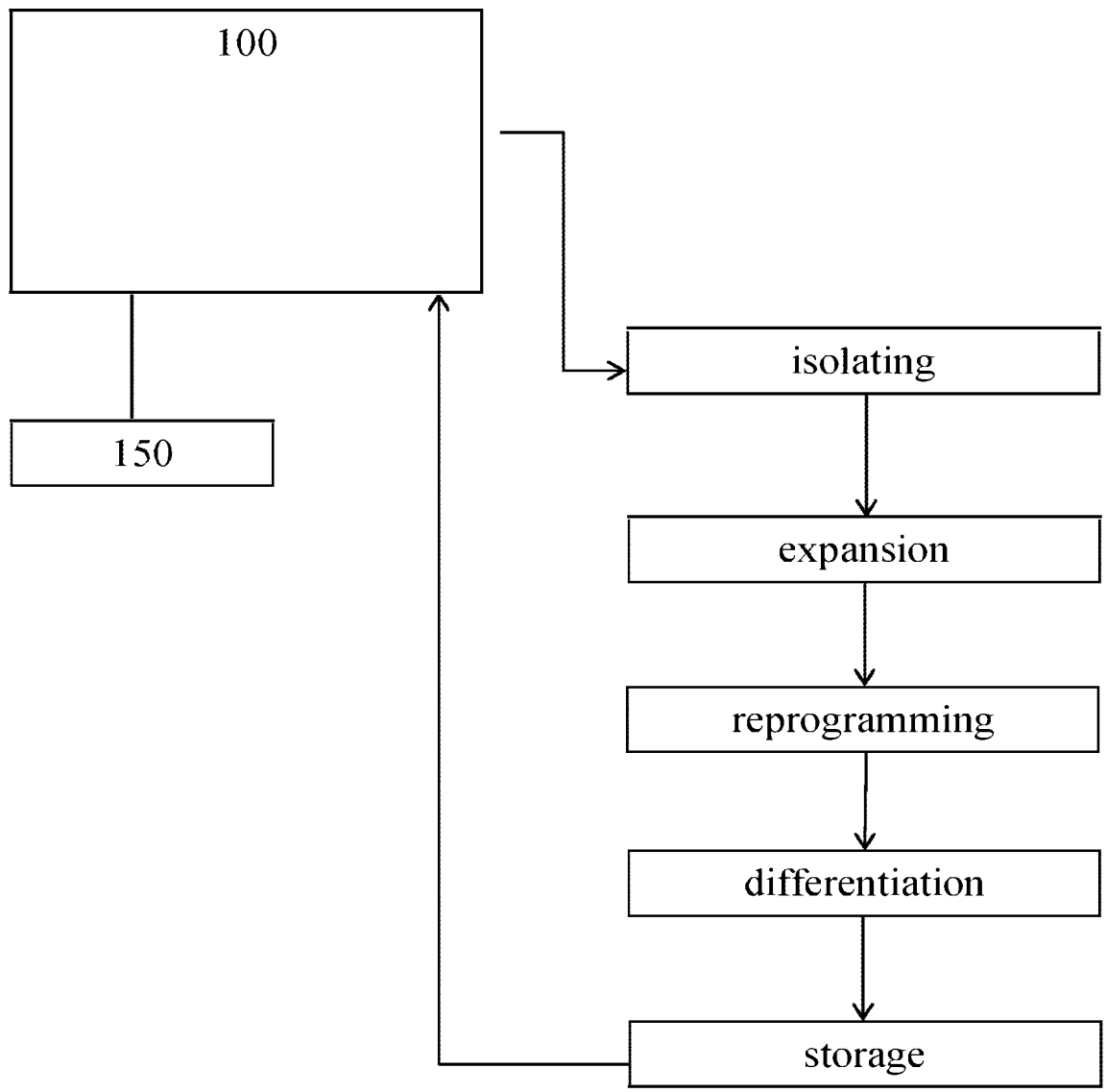
FIG. 1 is a schematic diagram of a microfluidic system in one embodiment of the invention.

The present invention provides an integrated microfluidic system that utilizes microfluidic chip technology to process a patient sample and generate patient-specific reprogrammed cells and optionally differentiated cells of a specific cell type from the reprogrammed cells. The invention system greatly improves the efficiency and reproducibility of making standardized iPSC lines. Typically, researchers generate iPSCs by hand, which limits the cells utility due to researcher variability and an inability to generate large numbers of cells. The system circumvents these problems with a completely automated system from receipt of the tissue or cell sample to banking of stocks of well-defined iPSC lines. The system allows for consistency and invariability for generation of large numbers of cells from many donors, which will facilitate the use of iPSC technology.

The system utilizes one or more microfluidic units, which may be in the form of one or more individual microfluidic chips, to process a sample, generate reprogrammed cells and maintain the cells in a microfluidic chip (hoteling) format for later retrieval and differentiation. Differentiation and expansion is then performed to generate cells of a desired cell type. Overall the workflow methodology and system is ideal as a laboratory or hospital based system that will allow the generation of pluripotent cells from every patient for downstream diagnostic or therapeutic use.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present disclosure provides a microfluidic system for processing a biological sample. The system includes one or more microfluidic units operable to perform a number of sample processing steps such that cells from the sample, or cells derived from the sample, such as iPSCs, may be stored and catalogued and eventually utilized to treat a patient from which the sample was taken. In embodiments, iPSCs generated from adult cells isolated from a patient sample are differentiated into a desired cell type suitable for use to treat the patient.

As used herein "adult" means post-fetal, i.e., an organism from the neonate stage through the end of life, and includes, for example, cells obtained from delivered placenta tissue, amniotic fluid and/or cord blood.

As used herein, the term "adult differentiated cell" encompasses a wide range of differentiated cell types obtained from an adult organism, that are amenable to producing iPSCs using the instantly described automation system. Preferably, the adult differentiated cell is a "fibroblast." Fibroblasts, also referred to as "fibrocytes" in their less active form, are derived from mesenchyme. Their function includes secreting the precursors of extracellular matrix components including, e.g., collagen. Histologically, fibroblasts are highly branched cells, but fibrocytes are generally smaller and are often described as spindle-shaped. Fibroblasts and fibrocytes derived from any tissue may be employed as a starting material for the automated workflow system on the invention.

As used herein, the term, "induced pluripotent stem cells" or, iPSCs, means that the stem cells are produced from differentiated adult cells that have been induced or changed, i.e., reprogrammed into cells capable of differentiating into tissues of all three germ or dermal layers: mesoderm, endoderm, and ectoderm. The iPSCs produced do not refer to cells as they are found in nature.

Mammalian somatic cells useful in the present invention include, by way of example, adult stem cells, sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. In particular embodiments, fibroblasts are used. The term somatic cell, as used herein, is also intended to include adult stem cells. An adult stem cell is a cell that is capable of giving rise to all cell types of a particular tissue. Exemplary adult stem cells include hematopoietic stem cells, neural stem cells, and mesenchymal stem cells.

One advantage of the present invention is that it provides an essentially limitless supply of isogenic or syngeneic human cells suitable for transplantation, use in drug discovery assays, or for disease modeling. The iPSCs are tailored specifically to the patient, avoiding immune rejection. Therefore, it will obviate the significant problem associated with current transplantation methods, such as, rejection of the transplanted tissue, which may occur because of host versus graft or graft versus host rejection. When utilized for drug discovery the cells demonstrate each person's response to chemicals when used in drug discovery or their individual manifestation of diseases in disease models. Several kinds of iPSCs or fully differentiated somatic cells prepared from iPSCs derived from somatic cells derived from humans can be stored in an iPSC bank as a library of cells, and one kind or more kinds of the iPSCs in the library can be used for preparation of somatic cells, tissues, or organs that are free of rejection by a patient to be subjected to stem cell therapy.

The iPSCs of the present invention may be differentiated into a number of different cell types to treat a variety of disorders by methods known in the art. For example, iPSCs may be induced to differentiate into hematopoetic stem cells, muscle cells, cardiac muscle cells, liver cells, cartilage cells, epithelial cells, urinary tract cells, neuronal cells, and the like. The differentiated cells may then be transplanted back into the patient's body to prevent or treat a condition or used to advance medical research or in to develop drug discovery assays. Thus, the methods of the present invention may be used to as a treatment or to develop a treatment for a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, Huntington's disease, amyotrophic lateral sclerosis (ALS), lysosomal storage diseases, multiple sclerosis, spinal cord injuries, genetic disorders, and similar diseases, where an increase or replacement of a particular cell type/tissue or cellular de-differentiation is desirable.

The term "totipotency" refers to a cell with a developmental potential to make all of the cells in the adult body as well as the extra-embryonic tissues, including the placenta. The fertilized egg (zygote) is totipotent, as are the cells (blastomeres) of the morula (up to the 16-cell stage following fertilization).

The term "pluripotent" as used herein refers to a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve). A pluripotent cell has a lower developmental potential than a totipotent cell. The ability of a cell to differentiate to all three germ layers can be determined using, for example, a nude mouse teratoma formation assay. In some embodiments, pluripotency can also evidenced by the expression of embryonic stem (ES) cell markers, although the preferred test for pluripotency of a cell or population of cells generated using the compositions and methods described herein is the demonstration that a cell has the developmental potential to differentiate into cells of each of the three germ layers. In some embodiments, a pluripotent cell is termed an "undifferentiated cell." Accordingly, the terms "pluripotency" or a "pluripotent state" as used herein refer to the developmental potential of a cell that provides the ability for the cell to differentiate into all three embryonic germ layers (endoderm, mesoderm and ectoderm). Those of skill in the art are aware of the embryonic germ layer or lineage that gives rise to a given cell type. A cell in a pluripotent state typically has the potential to divide in vitro for a long period of time, e.g., greater than one year or more than 30 passages.

The term "multipotent" when used in reference to a "multipotent cell" refers to a cell that has the developmental potential to differentiate into cells of one or more germ layers, but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

The terms "stem cell" or "undifferentiated cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.). A stem cell is capable of proliferation and giving rise to more such stem cells while maintaining its developmental potential. In theory, self-renewal can occur by either of two major mechanisms. Stem cells can divide asymmetrically, which is known as obligatory asymmetrical differentiation, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered stem cells, the range of cell types each such stem cell can give rise to, i.e., their developmental potential, can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity may be natural or may be induced artificially upon treatment with various factors. Cells that begin as stem cells might proceed toward a differentiated phenotype, but then can be induced to "reverse" and re-express the stem cell phenotype, a term often referred to as "dedifferentiation" or "reprogramming" or "retrodifferentiation" by persons of ordinary skill in the art.

The term "embryonic stem cell" as used herein refers to naturally occurring pluripotent stem cells of the inner cell mass of the embryonic blastocyst (see, for e.g., U.S. Pat. Nos. 5,843,780; 6,200,806; 7,029,913; 7,584,479, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). Embryonic stem cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta, i.e., are not totipotent.

As used herein, the distinguishing characteristics of an embryonic stem cell define an "embryonic stem cell phenotype." Accordingly, a cell has the phenotype of an embryonic stem cell if it possesses one or more of the unique characteristics of an embryonic stem cell, such that that cell can be distinguished from other cells not having the embryonic stem cell phenotype. Exemplary distinguishing embryonic stem cell phenotype characteristics include, without limitation, expression of specific cell-surface or intracellular markers, including protein and microRNAs, gene expression profiles, methylation profiles, deacetylation profiles, proliferative capacity, differentiation capacity, karyotype, responsiveness to particular culture conditions, and the like. In some embodiments, the determination of whether a cell has an "embryonic stem cell phenotype" is made by comparing one or more characteristics of the cell to one or more characteristics of an embryonic stem cell line cultured within the same laboratory.

The term "somatic stem cell" is used herein to refer to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Each of these somatic stem cells can be characterized based on gene expression, factor responsiveness, and morphology in culture. Exemplary naturally occurring somatic stem cells include, but are not limited to, neural stem cells, neural crest stem cells, mesenchymal stem cells, hematopoietic stem cells, and pancreatic stem cells. In some aspects described herein, a "somatic pluripotent cell" refers to a somatic cell, or a progeny cell of the somatic cell, that has had its developmental potential altered, i.e., increased, to that of a pluripotent state by contacting with, or the introduction of, one or more reprogramming factors using the compositions and methods described herein.

The term "progenitor cell" is used herein to refer to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cell forming the body of an organism, as opposed to a germline cell. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated, pluripotent, embryonic stem cells—is a somatic cell: internal organs, skin, bones, blood, and connective tissue are all made up of somatic cells. In some embodiments the somatic cell is a "non-embryonic somatic cell," by which is meant a somatic cell that is not present in or obtained from an embryo and does not result from proliferation of such a cell in vitro. In some embodiments the somatic cell is an "adult somatic cell," by which is meant a cell that is present in or obtained from an organism other than an embryo or a fetus or results from proliferation of such a cell in vitro. Unless otherwise indicated, the compositions and methods for reprogramming a somatic cell described herein can be performed both in vivo and in vitro (where in vivo is practiced when a somatic cell is present within a subject, and where in vitro is practiced using an isolated somatic cell maintained in culture).

The term "differentiated cell" encompasses any somatic cell that is not, in its native form, pluripotent, as that term is defined herein. Thus, the term a "differentiated cell" also encompasses cells that are partially differentiated, such as multipotent cells, or cells that are stable, non-pluripotent partially reprogrammed, or partially differentiated cells, generated using any of the compositions and methods described herein. In some embodiments, a differentiated cell is a cell that is a stable intermediate cell, such as a non-pluripotent, partially reprogrammed cell. It should be noted that placing many primary cells in culture can lead to some loss of fully differentiated characteristics. Thus, simply culturing such differentiated or somatic cells does not render these cells non-differentiated cells (e.g. undifferentiated cells) or pluripotent cells. The transition of a differentiated cell (including stable, non-pluripotent partially reprogrammed cell intermediates) to pluripotency requires a reprogramming stimulus beyond the stimuli that lead to partial loss of differentiated character upon placement in culture. Reprogrammed and, in some embodiments, partially reprogrammed cells, also have the characteristic of having the capacity to undergo extended passaging without loss of growth potential, relative to parental cells having lower developmental potential, which generally have capacity for only a limited number of divisions in culture. In some embodiments, the term "differentiated cell" also refers to a cell of a more specialized cell type (i.e., decreased developmental potential) derived from a cell of a less specialized cell type (i.e., increased developmental potential) (e.g., from an undifferentiated cell or a reprogrammed cell) where the cell has undergone a cellular differentiation process.

In various embodiments, the system is configured to perform a series of processes in a directional workflow. The processes performed by the system include isolating cells, expanding isolated cells, reprogramming expanded cells, differentiating reprogrammed cells to a desired cell type, and storing cells.

In various embodiments, the system is configured to isolate cells from a biological sample. This includes separation and isolation of specific cells types. In embodiments, a biological sample may include pre-isolated cells in which case it is not necessary to perform the isolation step. Isolation and/or separation techniques performed in a microfluidic capacity are known in the art and may be utilized in the practice of the invention. Such techniques include, but are not limited to cell capture and separation methodologies.

A "biological sample" is a sample of biological material taken from a patient or subject that includes intact cells. Biological samples include samples taken from bodily fluids and tissues (e.g., from a biopsy) or tissue preparations (e.g., tissue sections, homogenates, etc.). A "bodily fluid" is any fluid obtained or derived from a subject suitable for use in accordance with the invention. Such fluids include whole blood, blood fractions such as serum and plasma, urine, sweat, lymph, feces, ascites, seminal fluid, sputum, nipple aspirate, post-operative seroma, wound drainage fluid, saliva, synovial fluid, ascites fluid, bone marrow aspirate, cerebrospinal fluid, nasal secretions, amniotic fluid, bronchoalveolar lavage fluid, pleural effusion, peripheral blood mononuclear cells, total white blood cells, lymph node cells, spleen cells, and tonsil cells. In embodiments the sample includes white blood cells or is a sample of isolated white blood cells.

The term "isolated cell" as used herein refers to a cell that has been removed from an organism in which it was originally found, or a descendant of such a cell. Optionally the cell has been cultured in vitro, e.g., in the presence of other cells. Optionally, the cell is later introduced into a second organism or re-introduced into the organism from which it (or the cell or population of cells from which it descended) was isolated.

The term "isolated population" with respect to an isolated population of cells as used herein refers to a population of cells that has been removed and separated from a mixed or heterogeneous population of cells. In some embodiments, an isolated population is a "substantially pure" population of cells as compared to the heterogeneous population from which the cells were isolated or enriched. In some embodiments, the isolated population is an isolated population of pluripotent cells which comprise a substantially pure population of pluripotent cells as compared to a heterogeneous population of somatic cells from which the pluripotent cells were derived.

In various embodiments, the system is also configured to perform a cell expansion step utilizing cells isolated from the sample. This is to ensure that there are a sufficient number of cells to perform downstream processes.

Once cells are expanded, the system includes functionality to reprogram the expanded cell, for example to generate iPSCs. The term "reprogramming" as used herein refers to a process that reverses the developmental potential of a cell or population of cells (e.g., a somatic cell). Stated another way, reprogramming refers to a process of driving a cell to a state with higher developmental potential, i.e., backwards to a less differentiated state. The cell to be reprogrammed can be either partially or terminally differentiated prior to reprogramming. In some embodiments of the aspects described herein, reprogramming encompasses a complete or partial reversion of the differentiation state, i.e., an increase in the developmental potential of a cell, to that of a cell having a pluripotent state. In some embodiments, reprogramming encompasses driving a somatic cell to a pluripotent state, such that the cell has the developmental potential of an embryonic stem cell, i.e., an embryonic stem cell phenotype. In some embodiments, reprogramming also encompasses a partial reversion of the differentiation state or a partial increase of the developmental potential of a cell, such as a somatic cell or a unipotent cell, to a multipotent state. Reprogramming also encompasses partial reversion of the differentiation state of a cell to a state that renders the cell more susceptible to complete reprogramming to a pluripotent state when subjected to additional manipulations, such as those described herein. Such manipulations can result in endogenous expression of particular genes by the cells, or by the progeny of the cells, the expression of which contributes to or maintains the reprogramming. In certain embodiments, reprogramming of a cell using the synthetic, modified RNAs and methods thereof described herein causes the cell to assume a multipotent state (e.g., is a multipotent cell). In some embodiments, reprogramming of a cell (e.g. a somatic cell) using the synthetic, modified RNAs and methods thereof described herein causes the cell to assume a pluripotent-like state or an embryonic stem cell phenotype. The resulting cells are referred to herein as "reprogrammed cells," "somatic pluripotent cells," and "RNA-induced somatic pluripotent cells." The term "partially reprogrammed somatic cell" as referred to herein refers to a cell which has been reprogrammed from a cell with lower developmental potential by the methods as disclosed herein, such that the partially reprogrammed cell has not been completely reprogrammed to a pluripotent state but rather to a non-pluripotent, stable intermediate state. Such a partially reprogrammed cell can have a developmental potential lower that a pluripotent cell, but higher than a multipotent cell, as those terms are defined herein. A partially reprogrammed cell can, for example, differentiate into one or two of the three germ layers, but cannot differentiate into all three of the germ layers.

The term a "reprogramming factor," as used herein, refers to a developmental potential altering factor, as that term is defined herein, such as a gene, protein, RNA, DNA, or small molecule, the expression of which contributes to the reprogramming of a cell, e.g. a somatic cell, to a less differentiated or undifferentiated state, e.g. to a cell of a pluripotent state or partially pluripotent state. A reprogramming factor can be, for example, transcription factors that can reprogram cells to a pluripotent state, such as SOX2, OCT3/4, KLF4, NANOG, LIN-28, c-MYC, and the like, including as any gene, protein, RNA or small molecule, that can substitute for one or more of these in a method of reprogramming cells in vitro. In some embodiments, exogenous expression of a reprogramming factor, using the synthetic modified RNAs and methods thereof described herein, induces endogenous expression of one or more reprogramming factors, such that exogenous expression of one or more reprogramming factors is no longer required for stable maintenance of the cell in the reprogrammed or partially reprogrammed state. "Reprogramming to a pluripotent state in vitro" is used herein to refer to in vitro reprogramming methods that do not require and/or do not include nuclear or cytoplasmic transfer or cell fusion, e.g., with oocytes, embryos, germ cells, or pluripotent cells. A reprogramming factor can also be termed a "de-differentiation factor," which refers to a developmental potential altering factor, as that term is defined herein, such as a protein or RNA, that induces a cell to de-differentiate to a less differentiated phenotype, that is a de-differentiation factor increases the developmental potential of a cell.

Methods for transfecting and transforming or reprogramming adult cells to form iPSC lines are generally known, e.g., Takahashi et al., 2007 Cell, 131: 861-872, 2007, Yu et al., 2007, Science, vol. 318, pp. 1917-1920. iPSC are induced from somatic cells with reprogramming factors. Reprogramming factors are contemplated to include, e.g., transcription factors. The method for reprogramming adult cells includes, e.g., introducing and expressing a combination of specific transcription factors, e.g., a combination of Oct3/4, Sox2, Klf4 and c-Myc genes. Others have demonstrated that other transcription factors may be employed in transforming or reprogramming adult cells. These other transcription factors include, e.g., Lin28, Nanog, hTert and SV40 large T antigen as described, for example, by Takahashi et al., 2006 Cell, 126: 663-676 and Huiqun Yin, et al. 2009, Front. Agric. China 3(2): 199-208, incorporated by reference herein.

iPSCs can also be generated using direct introduction of RNAs into a cell, which, when translated, provide a desired protein or proteins. Higher eukaryotic cells have evolved cellular defenses against foreign, "non-self," RNA that ultimately result in the global inhibition of cellular protein synthesis, resulting in cellular toxicity. This response involves, in part, the production of Type I or Type II interferons, and is generally referred to as the "interferon response" or the "cellular innate immune response." The cellular defenses normally recognize synthetic RNAs as foreign, and induce this cellular innate immune response. In certain aspects where the ability to achieve sustained or repeated expression of an exogenously directed protein using RNA is hampered by the induction of this innate immune response, it is desirable to use synthetic RNAs that are modified in a manner that avoids or reduces the response. Avoidance or reduction of the innate immune response permit sustained expression from exogenously introduced RNA necessary, for example, to modify the developmental phenotype of a cell. In one aspect, sustained expression is achieved by repeated introduction of synthetic, modified RNAs into a target cell or its progeny. The inventive methods include natural or synthetic RNAs.

The natural, modified, or synthetic RNAs in one aspect, can be introduced to a cell in order to induce exogenous expression of a protein of interest in a cell. The ability to direct exogenous expression of a protein of interest using the modified, synthetic RNAs described herein is useful, for example, in the treatment of disorders caused by an endogenous genetic defect in a cell or organism that impairs or prevents the ability of that cell or organism to produce the protein of interest. Accordingly, in some embodiments, compositions and methods comprising the RNAs described herein can be used for the purposes of gene therapy.

The RNAs described can advantageously be used in the alteration of cellular fates and/or developmental potential. The ability to express a protein from an exogenous RNA permits either the alteration or reversal of the developmental potential of a cell, i.e., the reprogramming of the cell, and the directed differentiation of a cell to a more differentiated phenotype. A critical aspect in altering the developmental potential of a cell is the requirement for sustained and prolonged expression of one or more developmental potential altering factors in the cell or its immediate progeny. Traditionally, such sustained expression has been achieved by introducing DNA or viral vectors to a cell. These approaches have limited therapeutic utility due to the potential for insertional mutagenesis.

One of the areas that can most benefit from the ability to express a desired protein or proteins over a sustained period of time from exogenous RNAs as described herein is the generation of pluripotent or multipotent cells from cells initially having a more differentiated phenotype. In this aspect, RNAs encoding a reprogramming factor or factors are used to reprogram cells to a less differentiated phenotype, i.e., having a greater developmental potential.

In some embodiments of this aspect and all such aspects described herein, the synthetic, modified RNA molecule comprises at least two modified nucleosides. In one such embodiment, the two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I). In one such embodiment of this aspect and all such aspects described herein, the at least two modified nucleosides are 5-methylcytidine (5mC) and pseudouridine. (see e.g., Rossi US 2012/0046346, herein incorporated by reference).

Genes, proteins or RNA used in the methods of the invention include but are not limited to OCT4, SOX1, SOX 2, SOX 3, SOX15, SOX 18, NANOG, KLF1, KLF 2, KLF 4, KLF 5, NR5A2, c-MYC, 1-MYC, n-MYC, REM2, TERT, and LIN28.

It has also been shown that a single transcription factor may be employed in reprogramming adult fibroblasts to iPSCs with the addition of certain small molecule pathway inhibitors. Such pathway inhibitors include e.g., the transforming growth factor-beta (TGFb) pathway inhibitors, SB431542 (4-[4-(1,3-benzodioxol-5-yl)-5-(2-pyridinyl)-1H-imidazol-2-yl]-benzamide), and A-83-01 [3-(6-Methyl-2-pyridinyl)-N-phenyl-4-(4-quinolinyl)-1H-pyrazole-1-carbothioamide], the extracellular signal-regulated kinases (ERK) and microtubule-associated protein kinase (MAPK/ERK) pathway inhibitor PD0325901 (N-[(2R)-2,3-dihydroxypropoxy]-3,4-difluoro-2-[(2-fluoro-4-iodophenyl)amino]-benzamide), the GSK3 inhibitor CHIR99021 [6-((2-((4-(2,4-Dichlorophenyl)-5-(4-methyl-1H-imidazol-2-yl)pyrimidin-2-yl)amino)ethyl)amino)nicotinonitrile] which activates Wnt signaling by stabilizing beta-catenin, the lysine-specific demethylase1 Parnate (a/k/a tranylcypromine), the small molecule activator of 3'-phosphoinositide-dependent kinase-1 (PDK1) PS48 [(2Z)-5-(4-Chlorophenyl)-3-phenyl-2-pentenoic acid], the histone deacetylase (HDAC) inhibitors sodium butyrate and valproic acid, small molecules that modulate mitochondrial oxidation (e.g., 2,4- dinitrophenol), glycolytic metabolism (fructose 2,6-bisphosphate and oxalate), HIF pathway activation (N-oxaloylglycine and Quercetin) Zhu et al., 2010, *Cell Stem Cell* 7: 651-655, incorporated by reference herein it its entirety. Zhu et al showed that Oct4 combined with Parnate and CHIR99021 was sufficient to reprogram adult human epidermal keratinocytes.

Although individual protocols differ, a general reprogramming protocol consists of expanding differentiated adult cells from tissue samples, e.g., skin biopsies and contacting them with reprogramming factors as discussed above, e.g., infecting them, i.e., transfecting, with e.g., expression vectors, such as viral constructs containing transcripts for pluripotent transcription factors. The fibroblasts are obtained by art-known methods, e.g., by mechanically disrupting the tissue followed by enzymatic dissociation to release the fibroblasts, and culturing the fibroblasts by art-known methods, e.g., as described by Dimos et. al., 2008, *Science* Vol. 321 (5893): 1218-1221.

While illustrative aspects of the invention use vectors, e.g., viral vectors, plasmid vectors, in some aspects vectors are not required for transfection techniques, including those transferring mRNA molecules to cells.

Transfection of the fibroblasts with an expression vector is carried out according to instructions provided with the desired vector. After a time (e.g., ranging from about 2 to about 10 days post-transfection), the cells are dissociated and contacted with fluorescent tagged antibodies raised against the $CD13^{NEG}$, $SSEA4^{POS}$ and $Tra-1-60^{POS}$ surface markers. The dissociated and antibody-labeled cells are then resuspended in a phosphate buffered saline solution and moved to an automated sorting and isolation of iPSC clones. Surface marker positive cells are sorted by tag color or absence thereof directly into sterile tubes containing tissue culture media or multiwell (6-96 well) tissue culture plates coated with MEFs or cell free biological matrices and cultured until formation of visible colonies occurs.

Colonies are then further confirmed as iPSC by light microscopic inspection of the resulting clones or optionally by microscopic fluorescence inspection of clones labeled with fluorescent tagged antibodies. Optionally, in certain embodiments, one or more of the vectors also insert a green fluorescence protein (GFP) expression marker, for convenience in sorting and identification. Several individual colonies possessing morphological characteristics consistent with pluripotent ES cell lines are plucked from cultures and expanded individually to form monoclonal cultures.

In one preferred embodiment of the inventive system, the treated cells are subjected to genetic analysis to provide early confirmation and identification of iPSCs. Preferably, the genetic analysis is conducted by Southern blot, but other art-known methods may be employed which include but are not limited to MicroArray, NanoString, quantitative real time PCR (qPCR), whole genome sequencing, immunofluorescence microscopy, flow cytometry. Detection of enzymatic activity of alkaline phosphatase, positive expression of the cell membrane surface markers SSEA3, SSEA4, Tra-1-60, Tra-1-81 and the expression of the KLF4, Oct3/4, Nanog, Sox2 transcription factors in reprogrammed human fibroblasts confirms that a clone is an iPSC. Preferably, all of the markers are present.

Any art-known transfection vector may be employed as a reprogramming factor, including, e.g., an RNA such as mRNA, microRNA, siRNA, antisense RNA and combinations thereof. Other expression vectors that may be employed include, e.g., a retrovirus, a lentivirus, an adenovirus, an adeno associated virus, a herpes virus, a Sindbis virus, a pox virus, a bacula virus, a bacterial phage, a Sendai virus and combinations thereof. Preferably, an employed vector is a non-replicative vector such as, e.g., Sendai virus vectors engineered to be nonreplicative. The preferred Sendai virus vector, while incapable of replication, remains capable of productive expression of nucleic acids encoding protein(s) carried by the vector, thereby preventing any potential uncontrolled spread to other cells or within the body of a vaccinee. This type of Sendai vector is commercially available as a CytoTune™-iPSC Sendai viral vector kit (DNAVEC, DV-0301).

Any art-known transfection method may be employed to insert such vectors into the adult fibroblasts, including, e.g., electroporation, gene gun, and the like. Chemical transfection is optionally conducted by means of a transfecting agent e.g., a polymer, calcium phosphate, a cationic lipid, e.g., for lipofection, and the like. Cell penetrating peptides are also optionally employed to carry vectors or other agents into the adult fibroblast cells. In brief, cell-penetrating peptides include those derived from proteins, e.g., protein transduction domains and/or amphipathic peptides that can carry vectors or other agents into the cell include peptides. The subject of cell-penetrating peptides has been reviewed, e.g., by Heitz et al., 2009 *British Journal of Pharmacology,* 157: 195-206, incorporated by reference herein in its entirety. Other cell penetrating peptides are art-known, and are disclosed by Heitz, Id. Other cell-penetrating technologies including, e.g., liposomes and nanoparticles, are also contemplated to be employed in the methods of the present invention. Liposomes and nanoparticles are also described by Heitz, Id.

Antibodies can be employed in order to identify the transformed cells. Four antibodies against stem cell specific surface proteins are commonly used to identify and characterize human pluripotent stem cell populations; SSEA3, SSEA4, Tra-1-60 and Tra-1-81. The Stage Specific Embryonic Antigens 3 and 4 (SSEA3 and SSEA4) are two monoclonal antibodies which recognize sequential regions of a ganglioside present on human 2102Ep cells (Henderson et al., 2002 *Stem Cells* 20: 329-337; Kannagi et al., 1983, *Embo J* 2: 2355-2361). The Tra-1-60 and Tra-1-81 antibodies were originally raised against human embryonal carcinoma (EC) cells (P W et al., 1984, *Hybridoma* 3: 347-361) and have been shown to specifically recognize a carbohydrate epitope on a keratan sulfated glycoprotein identified as podocalyxin, a member of the CD34-related family of sialomucins (Badcock et al., 1999, *Cancer Research* 59: 4715-4719; Nielsen et al., 2007, PLoS ONE 2: e237; Schopperle and DeWolf, 2007, *Stem Cells* 25: 723-730). Several other surface markers have been shown to be expressed on ES cells and include CD326 or EpCam (Sundberg et al., 2009, *Stem Cell Res* 2: 113-124), CD24 (Heat Stable Antigen) and CD133 (Barraud et al., 2007, *Journal of Neuroscience Research* 85, 250-259) (Gang et al., 2007, *Blood* 109: 1743-1751). Chan et al., 2009, Id. reported that the identification of bona fide IPSc from fibroblasts undergoing reprogramming via four factor retro viral transduction can be achieved via live cell imaging and by the observation, over time, that fibroblasts lose expression of the cell surface markers CD13 and D7Fib, and gain expression of the pluripotent stem cell markers SSEA4 and Tra-1-60 (Chan et al., 2009, Id.).

Thus, the invention further provides iPSCs produced using the methods described herein, as well as populations of such cells. The reprogrammed cells of the present invention, capable of differentiation into a variety of cell types, have a variety of applications and therapeutic uses. The basic properties of stem cells, the capability to infinitely self-renew and the ability to differentiate into every cell type in the body make them ideal for therapeutic uses.

In various embodiments, the system further includes functionality to differentiate reprogrammed cells to a desired cell type. A major goal of stem cell technology is to make the stem cell differentiate into a desired cell type, i.e., directed differentiation or produce cells via transdifferentiation. Not only are the compositions and methods described herein useful for reprogramming cells, they are also applicable to this directed differentiation and transdifferentiation of cells to a desired phenotype. That is, the same technology described herein for reprogramming is directly applicable to the differentiation of the reprogrammed cell, or any other stem cell or precursor cell, for that matter, to a desired cell type.

A wide variety of additional cell types may be generated with differentiation, transdifferentiation and dedifferentiation. In the context of cell ontogeny, the term "differentiate", or "differentiating" is a relative term that refers to a developmental process by which a cell has progressed further down a developmental pathway than its immediate precursor cell. Thus in some embodiments, a reprogrammed cell as the term is defined herein, can differentiate to a lineage-restricted precursor cell (such as a mesodermal stem cell), which in turn can differentiate into other types of precursor cells further down the pathway (such as a tissue specific precursor, for example, a cardiomyocyte precursor), and then to an end-stage differentiated cell, which plays a characteristic role in a certain tissue type, and may or may not retain the capacity to proliferate further.

Differentiation is typically performed by contacting an iPSC with one or more differentiation factors. As used herein, the term "differentiation factor" refers to a developmental potential altering factor, as that term is defined herein, such as a protein, RNA, or small molecule, that induces a cell to differentiate to a desired cell-type, i.e., a differentiation factor reduces the developmental potential of a cell. In some embodiments, a differentiation factor can be a cell-type specific polypeptide, however this is not required. Differentiation to a specific cell type can require simultaneous and/or successive expression of more than one differentiation factor. In some aspects described herein, the developmental potential of a cell or population of cells is first increased via reprogramming or partial reprogramming using synthetic, modified RNAs, as described herein, and then the cell or progeny cells thereof produced by such reprogramming are induced to undergo differentiation by contacting with, or introducing, one or more synthetic, modified RNAs encoding differentiation factors, such that the cell or progeny cells thereof have decreased developmental potential.

As used herein, the term "without the formation of a pluripotent intermediate cell" refers to the transdifferentiation of one cell type to another cell type, preferably, in one step; thus a method that modifies the differentiated phenotype or developmental potential of a cell without the formation of a pluripotent intermediate cell does not require that the cell be first dedifferentiated (or reprogrammed) and then differentiated to another cell type. Instead, the cell type is merely "switched" from one cell type to another without going through a less differentiated phenotype. Accordingly, transdifferentiation refers to a change in the developmental potential of a cell whereby the cell is induced to become a different cell having a similar developmental potential, e.g., a liver cell to a pancreatic cell, a pancreatic alpha cell into a pancreatic beta cell, etc. The system and methods of the invention are well suited for transdifferentiation of cells.

In various aspects, illustrative genes encoding differentiation factors useful for differentiating, dedifferentiating, or transdifferentiating a cell include OCT4, NANOG, SOX2, SOX17, HNF4, GATA4, HHEX, CEBPβ, CEBPδ, PRDM16, MYOD1, NKX2.5, MEF2c, MYOCARDIN, RUNX2, PDX, NGN, SALL4 or SOX9, or combination thereof. The transcription factors encoded include Oct4, NANOG, Sox2, Sox9, Sox17, HNF4α2, HNF4α4, HNF4α7, HNF4α8, HNF4γ, GATA4, Hhex, CEBPβ, CEBPδ, PRDM16, MyoD1, Nkx2.5, Mef2c, Myocardin, Runx2-I, Pdx1, Ngn3, Sall4 or Runx2-II. For example, differentiation of mesoderm or fibroblasts to adipocytes, chondrocytes, osteocytes and myocytes may be performed using chimeric proteins including the following transcription factors: CEBPβ/CEBPδ (adipocytes), Sox9 (chondrocytes), Runx2 (osteocytes) and MyoD1 (myocytes).

Cell differentiation techniques performed in a microfluidic capacity are known in the art and may be utilized in the practice of the invention. Such techniques include those described in WO 2013/188748 which is incorporated herein by reference. WO 2013/188748 describes a microfluidic device for transdifferentiating cells from one cell type to another. The cells are cultured with one or more vector-free gene regulator oligonucleotides concurrently or in succession, and then harvested when cell markers or the morphology of the culture shows that transdifferentiation is complete. Suitable gene regular oligonucleotides include microRNAs and messenger RNAs that encode a differentiation factor. Conditions for transdifferentiation are optimized by dividing cells into different culture chambers of a microfluidic device. Cells are cultured with different additives in each chamber, and then compared.

Once differentiation is completed, the system has functionality for expanding the differentiated cells to generate sufficient numbers of a desired cell type for downstream use.

At any stage of processing, the system of the present invention has functionality for storing cells. For example, isolated cells may be stored, expanded cells may be stored, reprogrammed cells may be stored, differentiated cells may be stored. Storage may be under any suitable conditions for prolonging cell life, for example, by freezing cells at about −80° C. or below.

Furthermore, the system includes functionality for analyzing cells at any stage of processing to make qualitative and quantitative assessments of cells. Analysis may include any type of cellular analysis known in the art such as, by way of illustration, image analysis, cell number analysis, cell morphology analysis, polymerase chain reaction (PCR) analysis, sequence analysis, DNA analysis, RNA analysis, gene expression profiling, proteome analysis, metabolome analysis, immunoassays, nuclear exclusion analysis, or a combination thereof.

FIG. 1 illustrates an embodiment of the system which includes a single microfluidic unit 100 configured to perform each of the processing steps. The system is shown as also including a single computer module 140 which includes a computer memory module containing instructions for controlling the processing steps and a computer processor module configured to execute the instructions.

Figure 2:
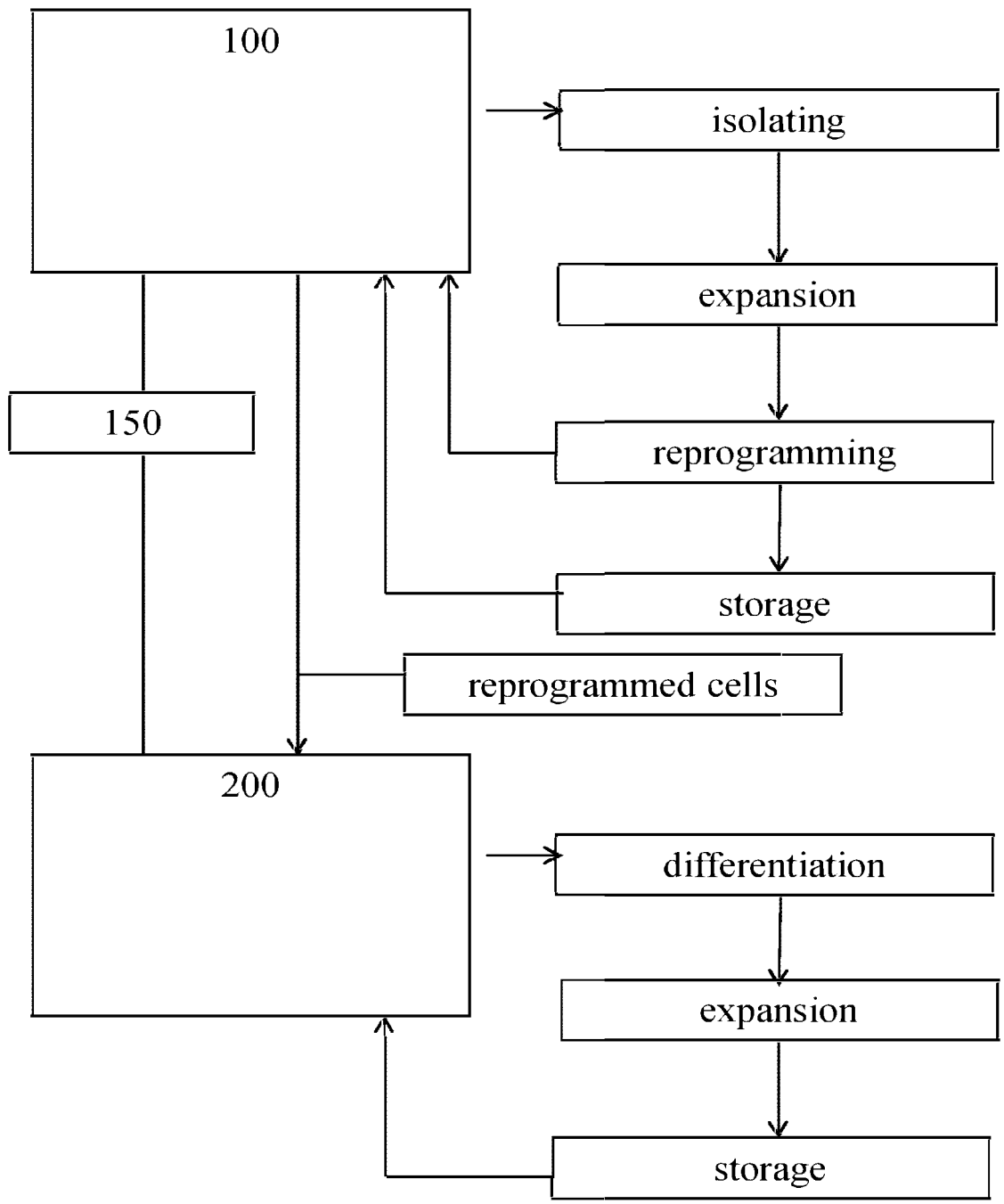
FIG. 2 is a schematic diagram of a microfluidic system in one embodiment of the invention.

It will be understood that the processing steps may be performed via one or more microfluidic units. For example, FIG. 2 shows an embodiment of a system having a first microfluidic unit 100 and a second microfluidic unit 200. Unit 100 is operable to perform cell isolation, cell expansion, cell reprogramming and optionally cell storage. Unit 200 is operable to perform cell differentiation and storage. Each unit is controlled by a single computer module 150.

It is envisioned that any number of processing steps may be performed by a single microfluidic unit. For example, each processing step may be performed by different microfluidic units. In the context of the present invention, a microfluidic unit may be formatted as a microfluidic chip which is designed such that a specific task may be performed on the chip, e.g., cell isolation, expansion, reprogramming and differentiation. It is also envisioned that a single microfluidic chip may include multiple microfluidic units, with different units arranged in different locations on the chip. In embodiments, the chip may be severable so that the microfluidic units may be separated at some stage during processing. For example, reprogramming may be performed by a microfluidic unit disposed on a first region of a chip and the storage of the reprogrammed cells may be performed by a microfluidic storage unit disposed on a second region of the chip. The two regions may be severable from one another such that the reprogramming region can be separated from the storage zone and only the storage zone be frozen.

To accomplish specific processing tasks, microfluidic units are designed to include a number of channels through which fluid flow is directed, the channels being formed in a nonporous substrate. The term "nonporous substrate" means a solid support material or matrix on top of which a microfluidic unit of the invention is created using photolithography or other suitable process. The material is typically poly dimethyl siloxane (PDMS) or poly methyl methacrylate (PMMA) or other suitable materials known in the art.

In various embodiments, the width of the flow channels can be from about 5 um to about 1000 um and, for larger width flow channels, can be about 100 um, at or between about 100 um and about 150 um, at or between about 150 um and 200 um, at or between about 200 um and 250 um, at or between about 250 um and about 300 um, at or between about 300 um and about 350 um, at or between about 350 um and about 400 um, at or between about 400 um and about 450 um, at or between about 450 um and about 500 um, at or between about 500 um and about 550 um, at or between about 550 um and 600 um, at or between about 600 um and about 650 um, at or between about 650 um and about 700 um, at or between about 700 um and about 750 um, at or between about 750 um and 800 um, at or between about 800 um and about 850 um, at or between about 850 um and about 900 um, at or between about 900 um and about 950 um, at or between 950 um and 1000 um. In many applications, a range of flow channel widths from about 75 um to about 125 um will be preferred. However, in certain instances, channel widths could exceed 1000 um. For narrower channels, the widths can be about 5 um or greater and about 100 um or smaller. Channel widths can be from about 10 um to about 75 um, from about 15 um to about 50 um, and from about 20 um to about 40 um. In some embodiments the channel width is about 5, 10, 15, 20, 25, 30, 35, 40, 45, 50, 55, 60, 65, 70, or 75 um. The height can be from about 5 um to about 100 um, from about 10 um to about 75 um, from about 15 um to about 50 um, and from about 20 to about 40 um. In some embodiments the channel height is about 5, 10, 15, 20, 25, 30, 35, 40, 45, 50, 55, 60, 65, 70, or 75 um. The cross sectional area can be from about 20 to about 13000 $um^2$, from about 50 to about 10000 $um^2$, from about 200 to about 8000 $um^2$, from about 250 to about 5000 $um^2$, from about 500 to about 3000 $um^2$, and in many embodiments, it is preferred to be from about 1400 to about 1600 $um^2$. In some embodiments the cross sectional area is about 500, 600, 700, 800, 900, 1000, 1100, 1200, 1300, 1400, 1500, 1600, 1700, 1800, 1900, or about 2000 $um^2$. The shape of the cross section of the individual channels of the matrix devices of this invention can be the same or different and can take different shapes such as square, rectangular, other polygonal, circular, elliptical, semicircular, semielliptical, and the like. The cross sectional shapes and areas can vary within the same channel and can be prepared by fabrication techniques described earlier and known in the art. Square or rectangular channel geometries are generally favored.

The present invention is described partly in terms of functional components and various processing steps. Such functional components and processing steps may be realized by any number of components, operations and techniques configured to perform the specified functions and achieve the various results. For example, the present invention may employ various biological samples, biomarkers, elements, materials, computers, data sources, storage systems and media, information gathering techniques and processes, data processing criteria, statistical analyses, regression analyses and the like, which may carry out a variety of functions. In addition, although the invention is described in the medical diagnosis context, the present invention may be practiced in conjunction with any number of applications, environments and data analyses; the systems described are merely exemplary applications for the invention.

Methods for processing according to various aspects of the present invention may be implemented in any suitable manner, for example using a computer program operating on the computer system. An exemplary system according to various aspects of the present invention is implemented in conjunction with a computer system, for example a conventional computer system comprising a processor and a random access memory, such as a remotely-accessible application server, network server, personal computer or workstation. The computer system also suitably includes additional memory devices or information storage systems, such as a mass storage system and a user interface, for example a conventional monitor, keyboard and tracking device. The computer system may, however, comprise any suitable computer system and associated equipment and may be configured in any suitable manner. In one embodiment, the computer system comprises a stand-alone system. In another embodiment, the computer system is part of a network of computers including a server and a database.

The software required for receiving, processing, and analyzing information may be implemented in a single device or implemented in a plurality of devices. The software may be accessible via a network such that storage and processing of information takes place remotely with respect to users. The system according to various aspects of the present invention and its various elements provide functions and operations to facilitate biomarker analysis, such as data gathering, processing, analysis, reporting and/or diagnosis. The present system maintains information relating to samples and may also facilitate analysis and/or diagnosis. For example, in the present embodiment, the computer system executes the computer program, which may receive, store, search, analyze, and report information relating to analysis of cells. The computer program may comprise multiple modules performing various functions or operations, such as a processing module for processing raw data and generating supplemental data and an analysis module for analyzing raw data and supplemental data to cause the system to perform specific tasks.

The system may also provide various additional modules and/or individual functions. For example, the system may also include a reporting function, for example to provide information relating to the processing and analysis functions. The system may also provide various administrative and management functions, such as controlling access and performing other administrative functions.

It will be understood that all, or any portion of the process required to generate iPSCs or differentiated cells therefrom, may be performed using a microfluidic unit, or a similarly automated process in operable connection to a microfluidic unit of the system of the invention.

In various embodiments, the system of the disclosure may utilize, or be in operable communication with, one or more systems (Systems 1-8) described in the following workflow system as disclosed in U.S. Patent Application Publication No. 2013/0345094, which is incorporated herein by reference in its entirety.

The Workflow System

The workflow system is broken down into four independently-operated units:
(1) Quarantine Somatic Cell Isolation and Growth (System 1);
(2) Quarantine Assay (System 2);
(3) Thawing, Infection and Identification (Systems 3, 4, and 5); and
(4) Maintenance, QC, Expansion, and Freezing. (Systems 6, 7, and 8)

Additionally, an automated −80 storage and retrieval system for storing fibroblasts and final clones in 1.4 mL Matrix screw cap tubes, is part of the system. The systems, and the steps and operations that each unit will perform, will be described below.

System 1, Part A: Quarantine Somatic Cell Isolation and Growth Workflow, Biopsy Processing Pre-Mycoplasma Test
1. Technician will plate 40 biopsies per week in 6-well dishes;
2. 6-well plates will be maintained in quarantine incubator with 200-plate capacity;
3. Periodic confluency checks are performed on an integrated Cyntellect Celigo Cytometer.

The system components that may be used to perform these automated steps include by way of example, STARlet Manual Load, a Modular Arm for 4/8/12 ch./MPH, 8 channels with 1000 μl Pipetting Channels and an iSWAP Plate Handler, all available from Hamilton Science Robotics. If centerfuging is needed or desired, an Agilent VSpin Microplate Centerfuge can be used. The software may be Celigo API Software. The incubator may be a Cytomat Incubator. For plate handling a Cytomat 24 Barcode Reader, Cytomat 23 mm Stackers, and a Cytomat 400 mm transfer station may be used. For plate tilting, one may use a MultiFlex Tilt Module. The system controller may be a Dell PG with a Windows XP operating system. The carrier package may be a Q Growth Carrier Package.

System 1, Part B: Quarantine Growth Workflow, Mycoplasma Test
1. Retrieve from incubator to deck of Quarantine Growth STARlet, remove media from wells to plate for ELISA based mycoplasma test.
2. Manually transfer 96-well assay plates to Quarantine Assay STARlet.

System 1, Part C: Quarantine Growth Workflow, After Passing Mycoplasma Testing
1. Expanded fibroblasts distributed into multiple cryovials, capped, transferred to SAM-80° C.

The system components that may be used to perform these automated steps may be selected from the same components used in the Quarantine Growth Workflow, except a STARlet Auto Load may be used. A Spectramax L Reader may be used as a spectral acquisition device.

System 2: Quarantine Assay Workflow
1. Test using glow luminescence method, Lonza MycoAlert.
2. Perform luminescence plate read on spectral acquisition device.

The system components that may be used to perform these automated steps include STARlet Manual Load, a Modular Arm for 4/8/12 ch./MPH, 8 channels with 1000 μl Pipetting Channels and an iSWAP Plate Handler, all available from Hamilton Science Robotics. For luminescence assays the BioTek Synergy HT Reader may be used. The system controller may be a Dell PG with a Windows XP operating system. The carrier package may be a Q Growth Carrier Package.

Systems 3, 4, and 5: Thawing, Infection and Identification
Thawing Module & Infection Module
1. Retrieve cryotubes from SAM-80° C. (61, 190)
2. Thaw on warming block (122)
3. Decap (Hamilton Capper Decapper) (126)
4. Add media to dilute cryoprotectants (122)
5. Spin (128)
6. Resuspend in plating data (122)
7. Plate one sample per well of 6-well (62, 122)
8. Move to incubator (130, 132)
9. Fibroblasts recover for about 3-4 days
10. Confluence check on Cyntellect Celigo Cytometer (124)
11. Fibroblast passaging of all wells on the same day for reprogramming (122)
12. In batches, trypsin passage wells (122)
13. Count cells on Cyntellect Celigo Cytometer (124)
14. Plate a defined number per well on one-to-three wells of a 24-well plate consolidating samples onto as few as 24-well plates as possible (64, 122)
15. Return plates to the incubator overnight (130, 132)
16. Retrieve plates and thaw virus in tube format and add to each well of the fibroblasts in the 24-well plates (130, 122)
17. Daily partial media exchanges (122)

Magnetic Sorting Module
18. Harvest cultures with accutase to single-cell suspension (134)
19. Dilute in staining buffer (134)
20. Stain with magnetic beads against fibroblast surface marker (134)
21. Wash step (134)
22. Apply to magnet (for Dynal beads) or column (for Miltenyi system) (134, 136)
23. Retrieve non-magnetic fraction to new wells (134)
24. Count cells on Cyntellect Celigo Cytometer (124)
25. Dilute to appropriate cell density for delivering 1-10 cells per well to 96-well plate in passaging media (66, 134)
26. Retrieve new Matrigel or matrix-coated 96-well plate from 4° C. incubator (142)
27. Distribute cells to 96-well matrix plates, number based on cell count for example, two per plates per infection (66, 134)
28. Return plates to incubator (132)
29. Daily partial media exchanges (122)

Colony Identification Module
30. Retrieve 96-well plates from incubator to Colony identification liquid handler (66, 132, 138)
31. Perform live cell stain with pluripotency surface marker (138)

32. Image on Cyntellect Celigo Cytometer (140)
33. Identify wells with a single-marker positive colony that has a sharp colony border (140)
34. Techs review hits and select 6 per original sample for passage and retrieve plate and positive well IDs.
35. Cherry-pick wells with single positive colonies (138)
36. Retrieve new Matrigel or matrix coated 96-well plate from 4° C. incubator (68, 142)
37. Harvest selected wells and passage to new 96-well matrix plate consolidating clones onto as few plates as possible and plating each in passaging media (68, 138)
38. Daily partial media exchanges (122)

The system components that may be used to perform these automated steps may be selected from the same components used in the Quarantine Growth Workflow with the addition of one or more CORE 96 PROBEHEAD II 1000 μl model probe heads.

Systems 6, 7, and 8: Maintenance, QC, Expansion, and Freezing

Maintenance Module

39. Will serially-passage clones 1:1 into new 96-well matrix-coated plates until colony density is high enough (68-72, 160)
40. Daily feeding of all plates with ~75% media exchange with 96-tip head (160)
41. Periodic monitoring of colony density and growth rates on Cyntellect Celigo Cytometer (166)
42. Plate replication to produce plates for QC of clones (74-86, 160)
43. Goal is to expand clones onto multiple plates for use in several QC assays to eliminate poorly-performing clones until left with two-to-three high-quality clones per original sample
44. Will also cherry-pick and re-array clones that pass QC steps as the poor clones are eliminated to consolidate clones onto as few plates as possible (80, 86, 160)
45. Daily feeding throughout this process (160)

QC Module

46. Harvest cells (74, 150)
47. Count cells (164)
48. Plate a defined cell number in V-bottom plates (range of 5000-10000 cells/well) in 2-6 replicates per line (84, 150)
49. Return to incubator—(1 g aggregation) (172)
50. Media exchange after two days (150)
51. Incubate for additional 12 days in incubator (172)
52. Partial media exchange every two days (150)
53. Transfer to nucleic acid prep station to remove media from wells leaving embryoid bodies in the well (84, 192)
54. Resuspend in RNA lysis buffer and combine and mix replicates for each sample and make plates available for analysis in Nanostring nCounter assay (84, 192)

Freezing Module

55. Begins with a 96-well plate after an expansion passage (88)
56. Incubate 6 days in incubator (172)
57. Partial media exchange every day (154)
58. Remove plate from incubator (88, 162)
59. Remove media (needs to be complete) (154)
60. Add cool Pre-freeze media (diluted matrigel in growth media) (154)
61. Incubate in incubator for 1 h (172)
62. Remove media (needs to be complete) (154)
63. Addition of cold freezing media—low volume (154)
64. Seal plate (88, 164
65. Samples taken off-line to −80° C. storage to freeze (190)
66. Store in vapor phase Liquid Nitrogen Cryovial Storage 67. Begins with a 96-well plate after an expansion passage (90)
68. Incubate 6 days (172)
69. Daily partial media exchanges (154)
70. Passage wells 1:1 to a 24-well plate (92, 154)
71. Incubate 6 days (172)
72. Daily partial media exchanges (154)
73. Passage wells 1:1 to a 6-well plate (94, 154)
74. Incubate 4-6 days (172)
75. Daily partial media exchanges (154)
76. Remove plate from incubator (162)
77. Partial media exchange with pre-freeze media (154)
78. Incubate in incubator for 1 h (172)
79. Harvest cells for freezing as for normal passage (154)
80. Move to matrix tubes, two-to-three tubes per well (96, 154)
81. Spin and remove media (168, 154)
82. Addition of cold freezing media (154)
83. Cap tubes (170)
84. Samples taken off-line to −80° C. storage (190)

Figure 3:
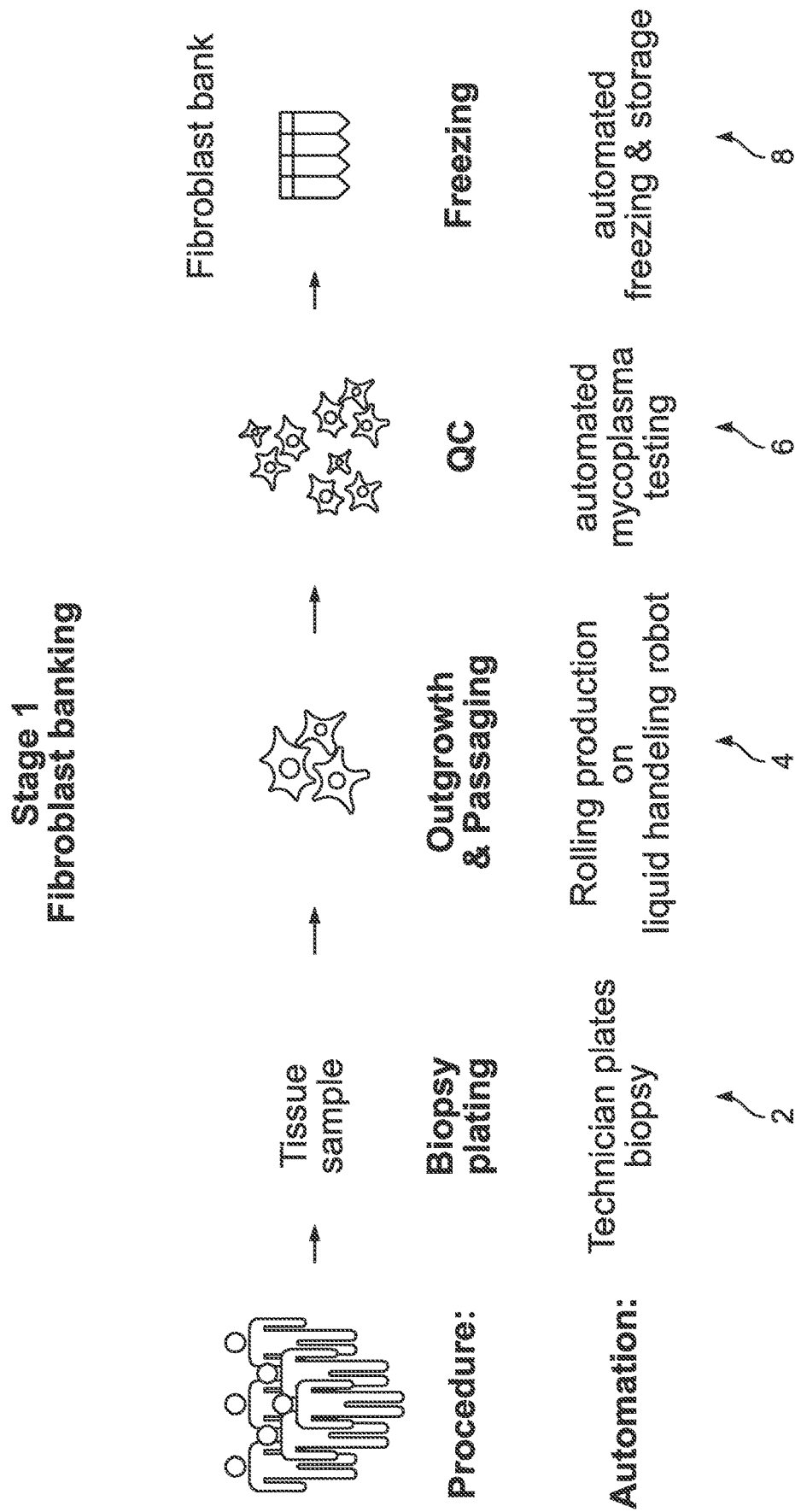
FIG. 3 shows steps for acquiring a fibroblast cell bank in one embodiment of the invention.

FIG. 3 shows the steps performed by System 1, including plating of a biopsy (2), outgrowth and passaging (4) (rolling production on liquid handling robot), QC (6) (automated testing for mycoplasma), and (8) automated freezing on liquid handling robot.

Figure 4:
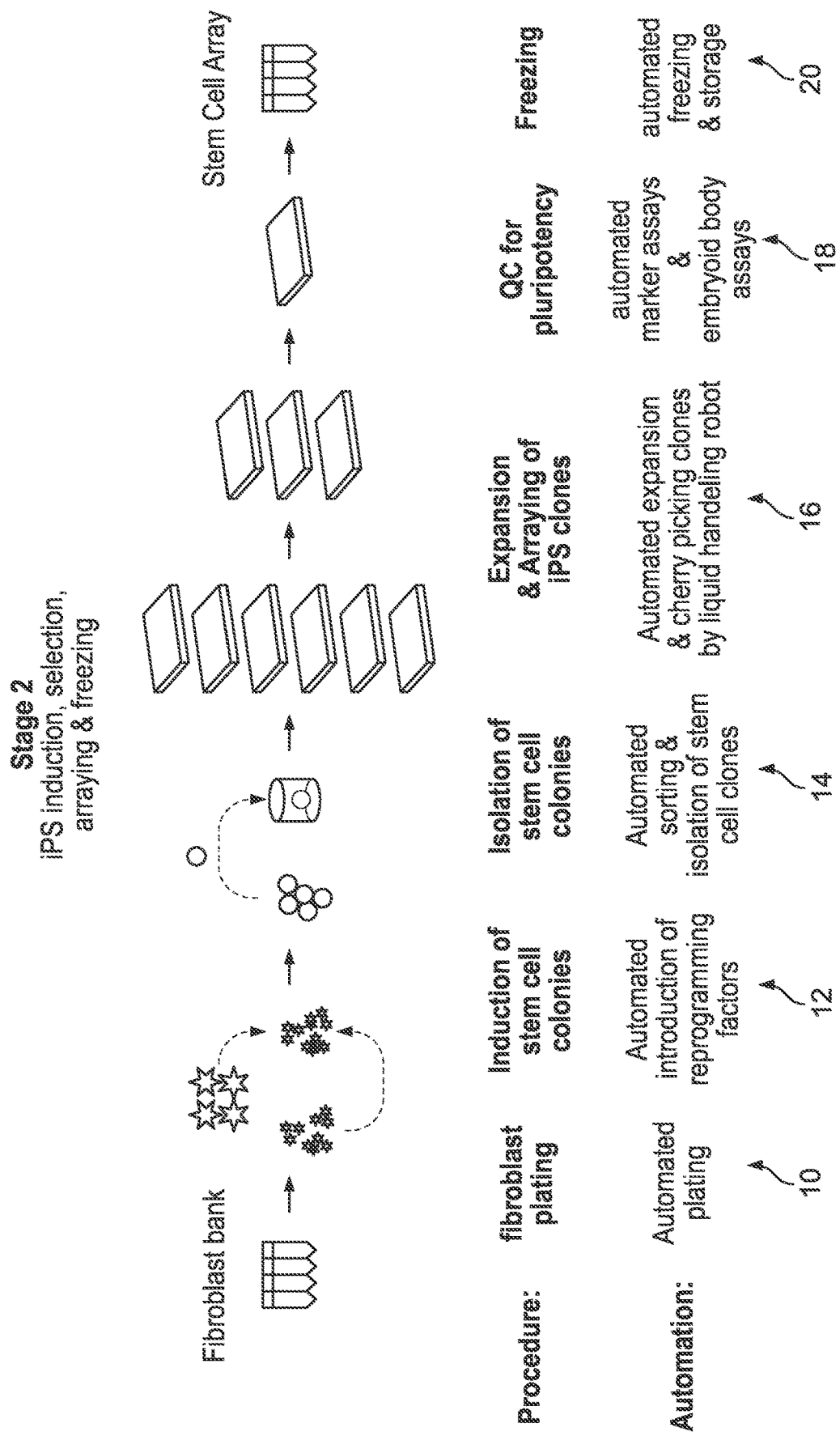
FIG. 4 shows steps for obtaining a stem cell array from a fibroblast bank in one embodiment of the invention.

FIG. 4 shows the steps performed by Systems 2, 3, and 4. Fibroblasts are plated by the automated system (10), reprogramming factors are introduced by the automated system (12), iPSCs are isolated by automated sorting and isolation (14), desired clones are selected and expanded by the automated system (16), automated quality checks (QC) for pluripotent status by marker assays and embryoid body assays (18), followed by automated freezing and storage of desired cells (20).

Figure 5:
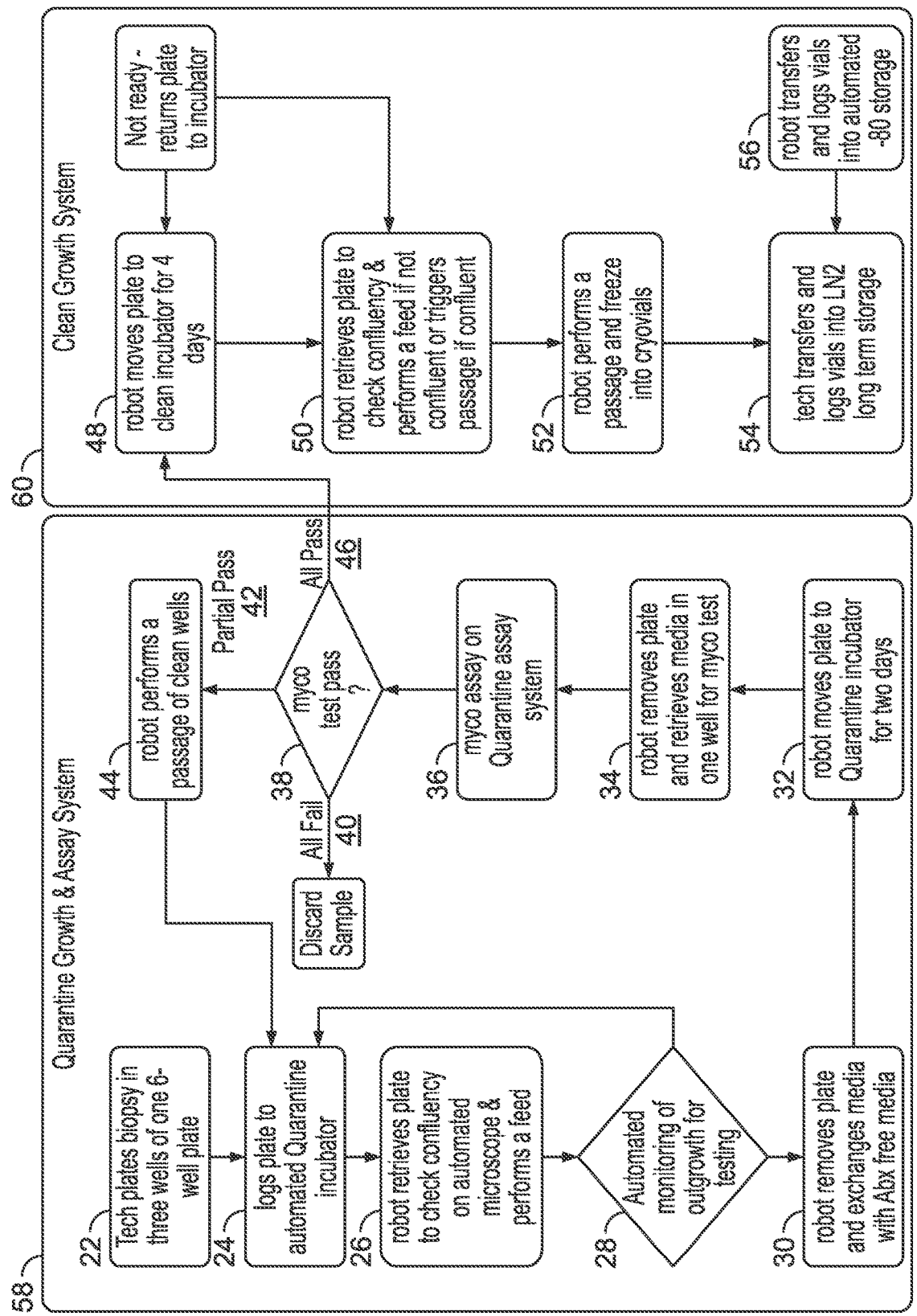
FIG. 5 is a flowchart showing steps in a system for producing iPSCs in one embodiment of the invention.

FIG. 5 is a flowchart showing the step (22) through (60) involved in System 1.

FIG. 5 illustrates an example of the workflow and decision tree for production of fibroblasts from biopsies. The workflow is divided into Quarantine (58) and Clean phases (60). As biopsies enter the facility, a technician plates biopsies in 6-well plates (22) and logs the plates into the automated incubator (24). After biopsies are given time to attach to the plate, the liquid handling robot retrieves the plates from the automated incubator to feed and check confluency of the outgrowths on an automated microscope (26). The plates are returned to the incubator and allowed to outgrow (28). The liquid handler removes the plate from the incubator and exchanges the media for antibiotic and antimycotic free media (30). The robot moves the plate to the incubator for another five days (32). The robot then removes the plate and retrieves media to daughter plates for mycoplasma test (34). The daughter plates are moved to the Quarantine Assay system for mycoplasma testing (36). A choice is then made based on a positive signal from the assay (38). If all wells of a 6-well plate fail with a positive mycoplasma assay result (40) they are discarded. If all wells of a 6-well plate are negative and free of mycoplasma, they are transferred out of quarantine into the clean growth system (46). If some wells are positive and some wells are negative, the negative wells are maintained in quarantine (42). The negative wells are passaged (44) to new plates, transferred to the incubator, and the source plates containing positive wells are discarded. These cultures proceed through steps to retest for mycoplasma (24, 26, 28, 30, 32, 34, 36, 38). Clean cultures are monitored for growth (50), passaged (52) and frozen in cryovials (54, 56).

Figure 6A:
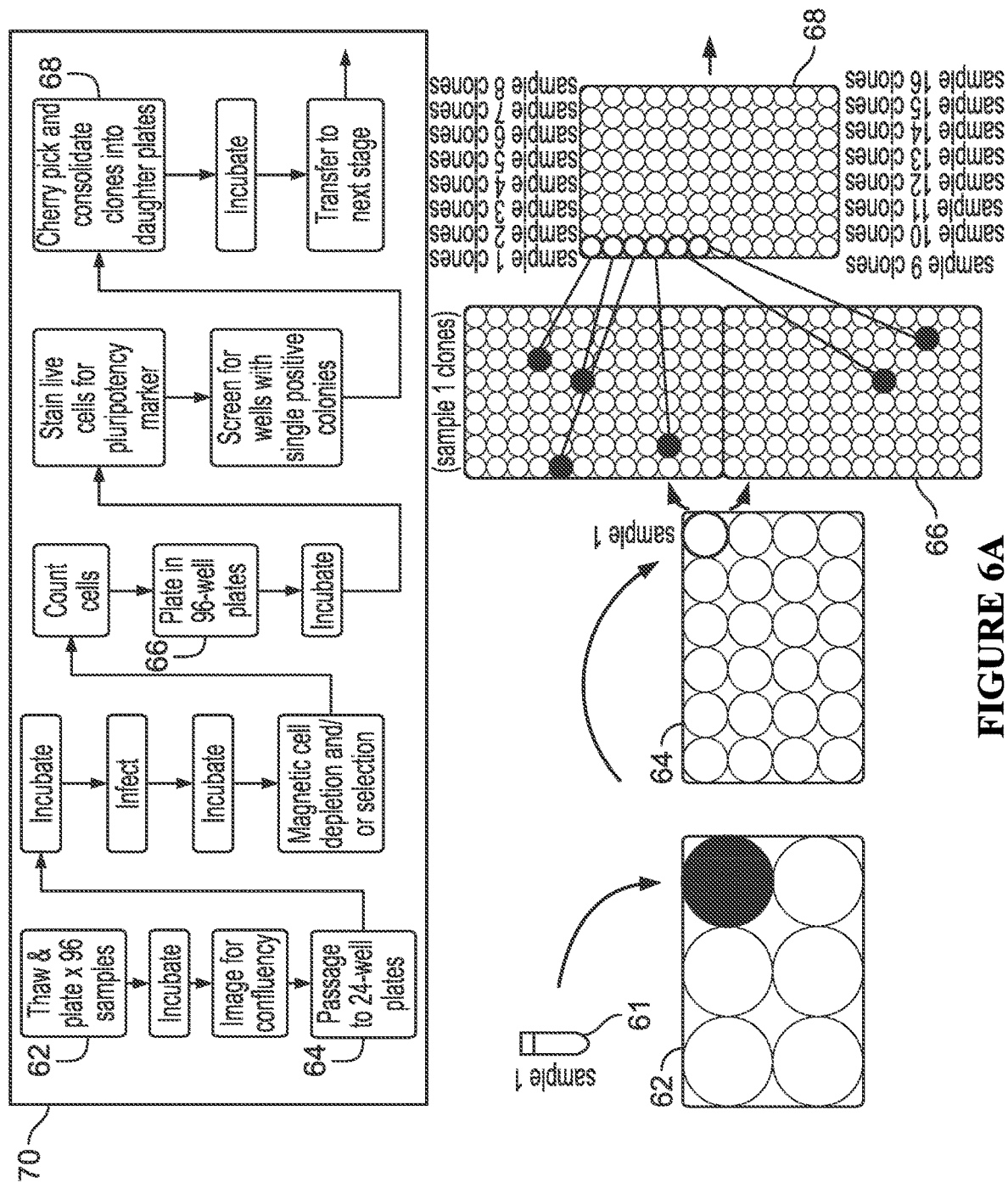
Figure 6C:
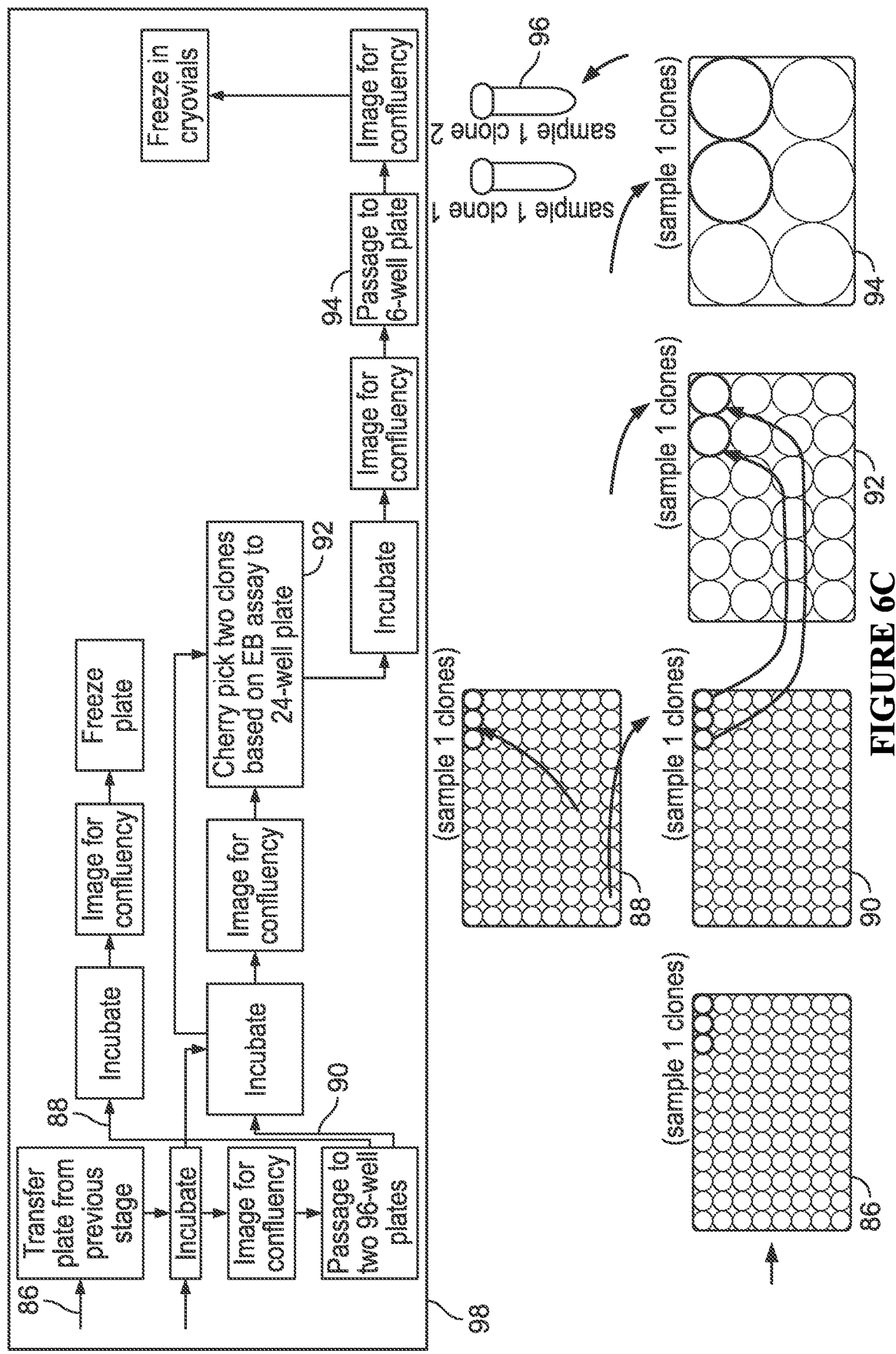

FIGS. 6A, 6B1, 6B2, and 6C illustrate an example of the flow of patient samples through multi-well tissue culture plates during the automated reprogramming process. At the top of each diagram, a flowchart describes the flow of procedures performed at each step of the workflow (70, 88, 98). At the bottom of each diagram, multi-well cell culture plates are shown with platemaps for example samples represented by shaded wells or groups of wells marked with sample labels (61-68, 72-86, 88-96). Transfer of a sample from plate-to-plate or well-to-well through the procedure is shown from left to right as indicated by arrows. As shown in FIG. 6A, the automated iPSC derivation process begins when patient samples and control fibroblast samples (61) are plated in individual wells of a 6-well plate (62). These are passaged at defined cell number into individual wells of a 24-well plate (64) for infection using viruses encoding reprogramming factors or other means of introducing reprogramming factors to the cells. In the next step, reprogrammed samples are depleted of non-reprogrammed cells by cell sorting or, as is preferred, using magnetic bead based enrichment and plated at clonal density in multiple wells in 96-well plates (66). Two such plates are shown in this example. In this example, 6 wells, as indicated by wells with a dot in the middle (66) are identified containing a single clone positive for a pluripotency surface marker as assayed by immunofluorescent analysis on automated imager. These clones are passaged and cherry picked to reformat the clones into a minimum number of 96-well plates (68). The example figure shows six clones per individual starting sample and indicates that clones from 16 starting sample can be arrayed onto a 96-well plate. To facilitate plate processing, this cherry picking step can be performed over multiple passages to consolidate the clones onto a minimum number of plates. As show in FIGS. 6B1 and 6B2, these clones are serially passaged until confluence of stem cell colonies within a well is achieved for each starting sample (72). Each plates' samples are then replicated onto duplicate plates (74-86), to allow for the quality control (6) and selection of clones that demonstrate appropriate stem cell characteristics. To begin the QC process, one plate is generated by the system for a Pluripotency quality control assay needed to determine pluripotent status of the individual clones (74) and one plate is generated for carrying forward in subsequent passages (76). The plate that is carried forward is passaged again into three plates (78, 80, 82) for further quality control and expansion. One plate is harvested for QC assays to characterize Karyotype and genetic diversity (78). A second plate (82) is passaged onto v-bottom plates to form embryoid bodies (84) for a QC assay that assesses differentiation capability of the iPS clones. The final plate (80) is carried forward for further expansion. Individual clones that do not pass quality control from previous pluripotency QC assays are not carried forward as shown by the "X" in the wells indicated in FIG. 6. In the example shown in FIG. 6B2, the consolidated plate (86) will contain iPS lines (or differentiated lines) from up to 32 individuals represented by 3 iPS clones per individual on a single 96 well plate or up to 96 individuals if represented by a single clone each. Remaining clones are consolidated onto as few plates as possible until one to three clones remain (86-92). As shown in FIG. 6C, these are expanded for cryopreservation while attached to the plate (88) or further expanded (92-94) and cryopreserved in cryovials (96). Any or all information from the pluripotency marker screen shown in FIG. 6A (70), and the quality control assays shown in FIG. 6B1 can be used alone or in combination to decide which clones to select for consolidation and arraying in the automated process.

Figure 7A:
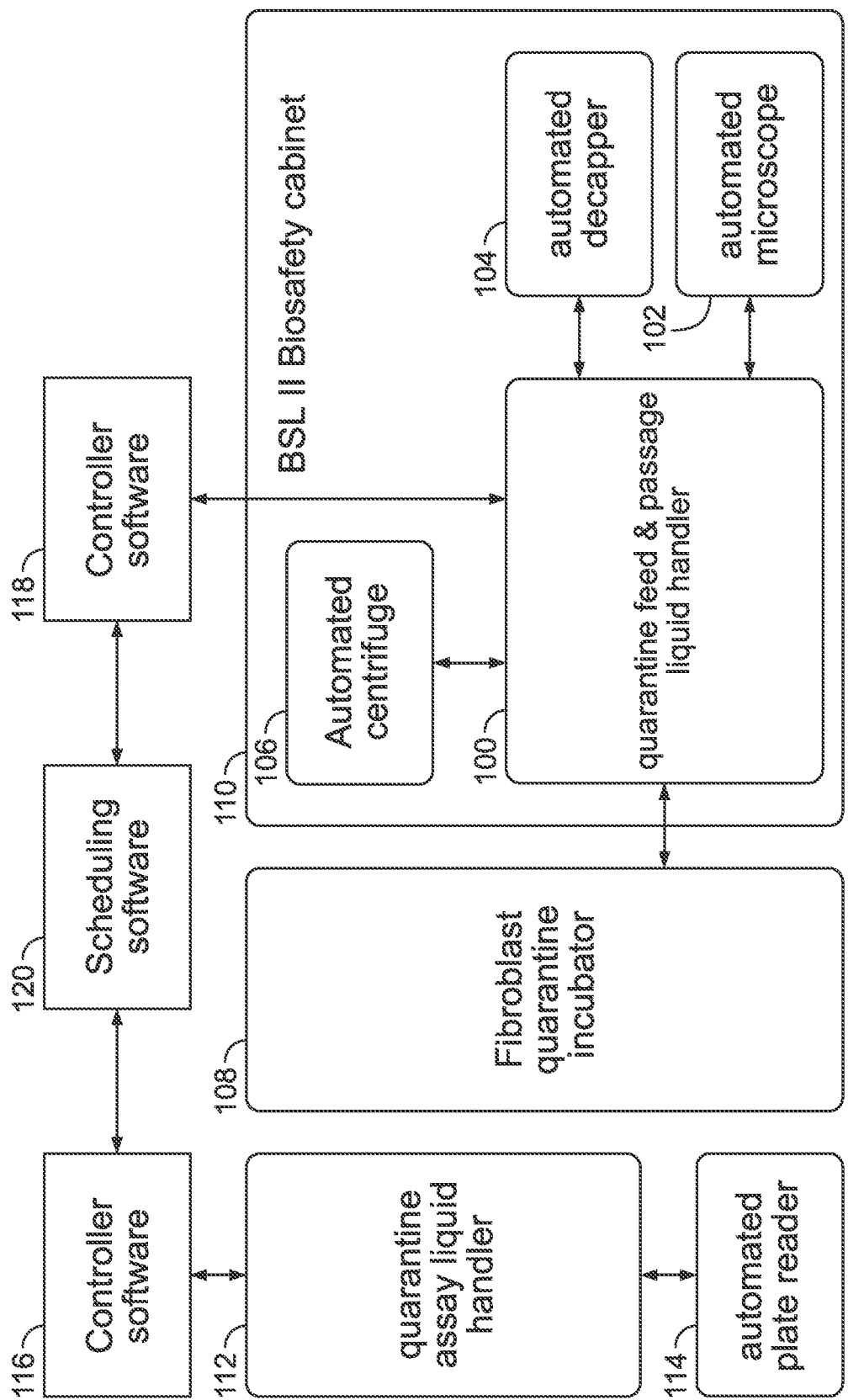
FIGS. 7A-7C show an example of an equipment configuration to accomplish the workflow in one embodiment of the invention.
Figure 7B:
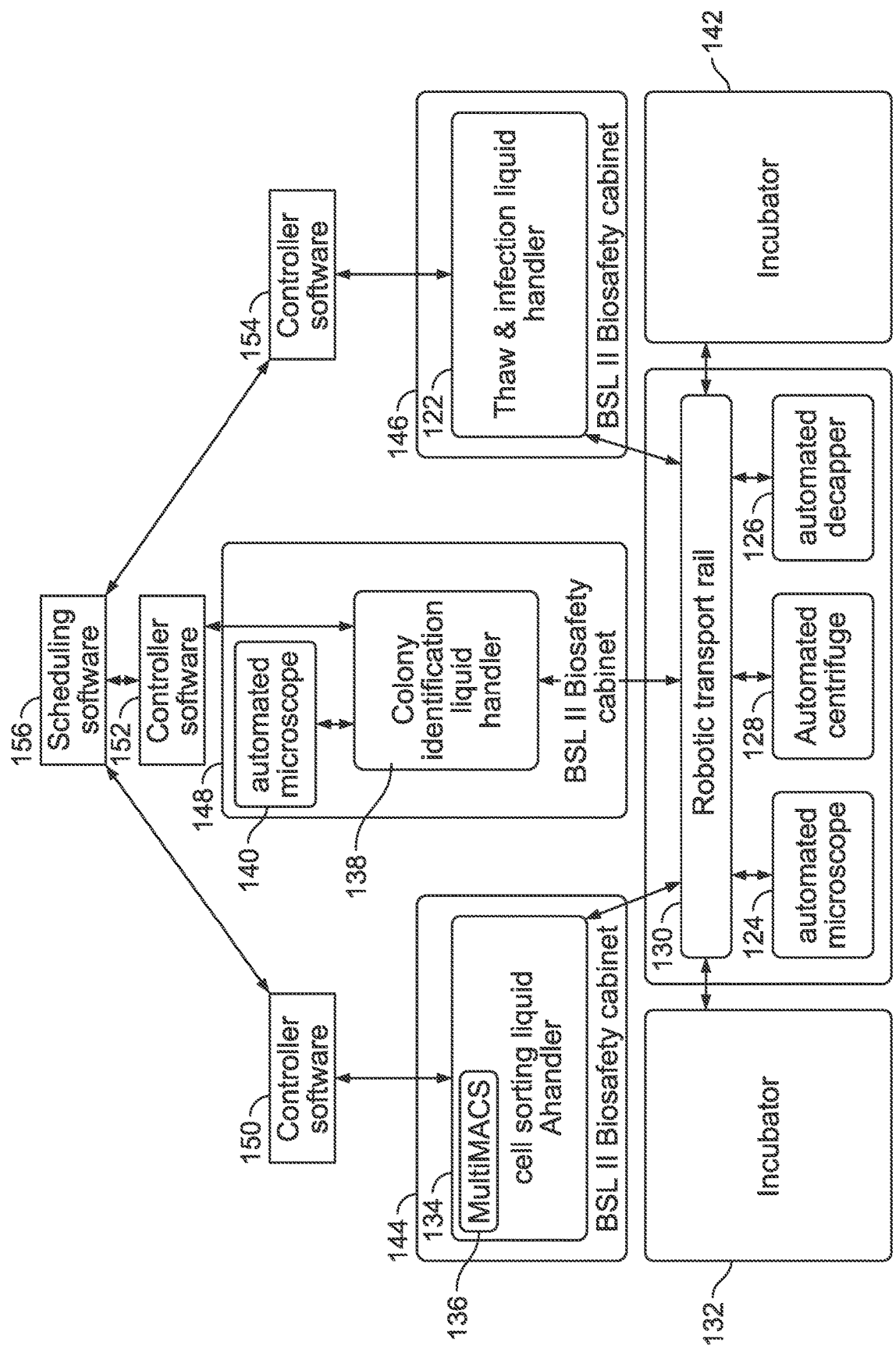
Figure 7C:
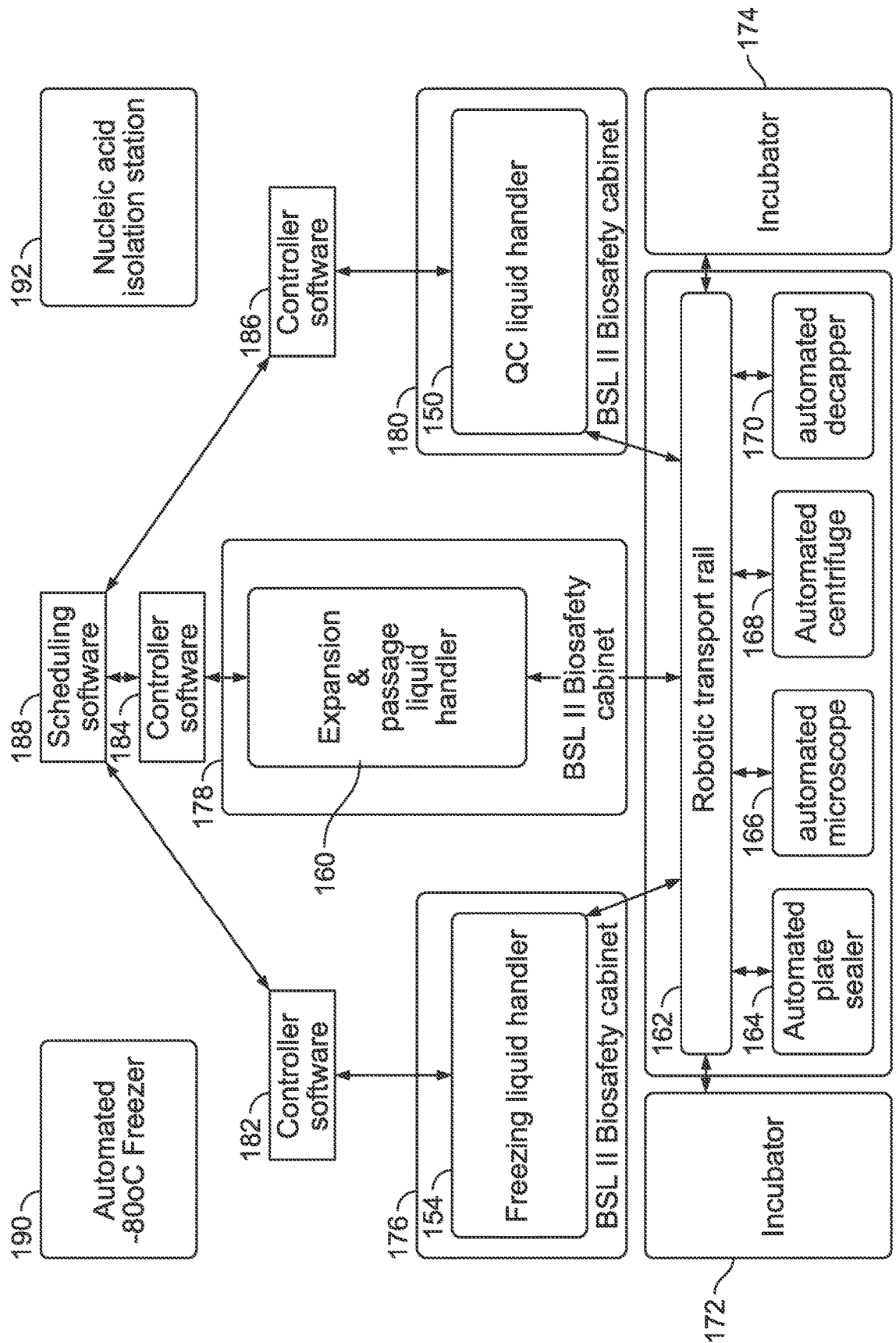

FIGS. 7A, 7B, 7C illustrate an example of the equipment configuration needed to accomplish the workflow in one embodiment of the invention. FIG. 7A shows a system configuration for the automated expansion and quality control of a fibroblast bank. FIG. 7B shows a system configuration for the automated thawing of patient samples, such as fibroblasts, automated introduction of reprogramming factors with the patient samples, such as fibroblasts, automated cell sorting with MultiMACS, and automated colony identification and reformatting. FIG. 7C shows a system configuration for the automated expansion of iPS clones, automated Embryoid Body production, and automated freezing.

As discussed herein, cells processed utilizing the system of the disclosure may be stored for downstream use. For example, processed cells of the invention may be utilized to treat a subject. For example, reprogrammed or differentiated cells may be utilized to treat a disease or disorder in subject. As such, the invention provides a method of treating a disease or disorder in a subject utilizing the microfluidic based system of the disclosure. The method includes: a) obtaining a sample from the subject; b) applying the sample to the system; c) processing the sample with the system; and d) administering processed cells to the subject.

In embodiments, the subject is healthy when the sample is obtained. The sample is processed to produce reprogrammed cells and the reprogrammed cells catalogued and stored. Once the subject is diagnosed with a disease and in need of medical treatment, the reprogrammed cells may be further processed to produce differentiated cells of a desired cell type which are then used to treat the subject. For some treatments, the reprogrammed cells may be used to treat the subject. Appropriate differentiated cells (of ectodermal, mesodermal or endodermal lineage) may be derived from iPSCs produced by the inventive methods. The mode of administration can be determined by a person of skill in the art depending on the type of organ/injury to be treated. For example, iPSCs or differentiated cells derived therefrom, may be administered by injection (as a suspension) or implanted on a biodegradable matrix.

The term "healthy", "normal" or "clinically normal" means the subject has no known or apparent or presently detectable disease or dysfunction correlated with a disease.

In another embodiment, the subject from which the sample is obtained has been diagnosed with, or as risk of having, a disease or disorder. The sample is processed to produce reprogrammed cells and the reprogrammed cells optionally stored. Once the subject medical treatment has been determined, the reprogrammed cells may be further processed to produce differentiated cells of a desired cell type which are then used to treat the subject. For some treatments, the reprogrammed cells may be used to treat the subject.

A "subject" is a member of any animal species, preferably a mammalian species, optionally a human. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology. The subject can be an apparently healthy individual, an individual suffering from a disease, or an individual being treated for a disease.

Also contemplated to be within the scope of the invention are compositions comprising iPSCs or differentiated cells, e.g., compositions employed as research tools, or as pharmaceutical compositions, comprising effective amounts of cells prepared by the system.

In addition, the invention relates to methods of testing pharmaceuticals by contacting iPSCs, transdifferentiated, or differentiated cells derived therefrom, for example, with one or more pharmaceutical agents of interest, and then detecting the effect of the applied pharmaceutical agent(s) on the contacted cells. For efficiency, pharmaceutical agent(s) are applied to a battery of iPSCs, or differentiated cells derived therefrom. The cells can vary in tissue source, in differentiated cell type, or allelic source, to allow identification of cells or tissue types that react favorably or unfavorably to one or more pharmaceutical agents of interest.

Further, the iPSCs produced by the inventive automated system may be used as a vehicle for introducing genes to correct genetic defects, such as osteogenesis imperfecta, diabetes mellitus, neurodegenerative diseases such as, for instance, Alzheimer's disease, Parkinson's disease, the various motor neuron diseases (MND), e.g., amyotrophic lateral sclerosis (ALS), primary lateral sclerosis (PLS), progressive muscular atrophy (PMA) and the like.

iPSCs produced by the inventive automated system may also be employed to provide specific cell types for biomedical research, as well as directly, or as precursors, to produce specific cell types for cell-based assays, e.g., for cell toxicity studies (to determine the effect of test compounds on cell toxicity), to determine teratogenic or carcinogenic effects of test compounds by treating the cells with the compound and observing and/or recording the compound's effects on the cells, e.g. effect on cellular differentiation.

Although the invention has been described with reference to the above example, it will be understood that modifications and variations are encompassed within the spirit and scope of the invention. Accordingly, the invention is limited only by the following claims.

What is claimed is:

1. A microfluidic system for processing a biological sample comprising:
    a) one or more microfluidic units operable to process the sample, the processing comprising:
        i) expanding isolated cells to produce a population of expanded cells;
        ii) reprogramming the isolated cells or the expanded cells to produce a population of reprogrammed cells; and
        iii) storing cells from one or more of (i) or (ii); and
    b) one or more computer memory modules containing instructions, and programmed for controlling one or more of processes (i)-(iii); and
    c) one or more computer processor modules programmed to execute the instructions,
wherein the one or more microfluidic units comprises a plurality of flow channels.

2. The system of claim 1, wherein the system is further operable to perform an analysis of the expanded cells of (i), the reprogrammed cells of (ii), or a combination thereof.

3. The system of claim 1, wherein the one or more microfluidic units is further operable to differentiate the reprogrammed cells to produce a cell of a desired cell type.

4. The system of claim 1, wherein the isolated cells are somatic cells.

5. The system of claim 1, wherein the isolated cells are white blood cells.

6. The system of claim 1, wherein the sample is selected from whole blood, blood fractions, serum, plasma, urine, sweat, lymph, feces, ascites, seminal fluid, sputum, nipple aspirate, post-operative seroma, wound drainage fluid, saliva, synovial fluid, ascites fluid, bone marrow aspirate, cerebrospinal fluid, nasal secretions, amniotic fluid, bronchoalveolar lavage fluid, pleural effusion, peripheral blood mononuclear cells, skin cells, total white blood cells, lymph node cells, spleen cells, skin biopsy, cord blood, cord tissue and tonsil cells.

7. The system of claim 1, wherein storing cells comprises freezing the cells.

8. The system of claim 1, further comprising a graphical user interface.

9. The system of claim 1, wherein the system comprises at least two, three, or four microfluidic units.

10. The system of claim 1, wherein the microfluidic units are disposed within a unitary housing.

11. The system of claim 1, wherein the isolated cells, the expanded cells, and/or the reprogrammed cells are stored on a microfluidic chip.

12. The system of claim 1, wherein the system further comprises a storage unit for storing the cells at −80° C. or less.

13. The system of claim 1, wherein the system is further operable to process and store sample data associated with stored cells.

14. The system of claim 1, wherein cells are stored as master and working cell banks.

15. The system of claim 1, wherein reprogramming cells comprises contacting the cells with one or more nuclear reprogramming factors.

16. A method for processing a biological sample comprising:
    a) applying the sample to the system according to claim 1; and
    b) processing the sample with the system, the processing comprising:
        i) expanding the isolated cells to produce a population of expanded cells;
        ii) reprogramming the isolated or expanded cells to produce a population of reprogrammed cells; and
        iii) storing cells from any of (i) or (ii), thereby processing the biological sample.

17. A method of treating a disease or disorder in a subject comprising:
    a) obtaining a sample from the subject;
    b) applying the sample to the system according to claim 1;
    c) processing the sample with the system, the processing comprising:
        i) expanding the isolated cells to produce a population of expanded cells;
        ii) reprogramming the isolated or expanded cells to produce a population of reprogrammed cells;
        iii) differentiating the reprogrammed cells to a desired cell type; and
        iv) storing cells from any of (i), (ii), or (iii); and
    d) administering the subject a cell of any of (i)-(iv), thereby treating the disease or disorder in the subject.

18. A pharmaceutical composition comprising cells processed by the system of claim 1, or a cellular fraction thereof.

19. A cell bank comprising one or more populations of cells processed by the system of claim 1.

20. The cell bank of claim 19, wherein each population is derived from a different sample.

21. The system of claim 1, wherein the system comprises at least one, two, three, or four microfluidic units in operable communication with a secondary device.

22. The system of claim 1, wherein the cells are pre-isolated from the biological sample prior to expanding.

* * * * *